(12) United States Patent
McFarland et al.

(10) Patent No.: US 9,988,409 B2
(45) Date of Patent: Jun. 5, 2018

(54) MULTI-DIMENSIONAL NETWORKS

(75) Inventors: Eric McFarland, Santa Barbara, CA (US); Omar Yaghi, Los Angeles, CA (US); Hexiang Deng, Los Angeles, CA (US); Dani Peri, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 1188 days.

(21) Appl. No.: 13/997,144

(22) PCT Filed: Dec. 21, 2011

(86) PCT No.: PCT/US2011/066648
§ 371 (c)(1),
(2), (4) Date: Nov. 4, 2013

(87) PCT Pub. No.: WO2012/088352
PCT Pub. Date: Jun. 28, 2012

(65) Prior Publication Data
US 2014/0205846 A1    Jul. 24, 2014

Related U.S. Application Data

(60) Provisional application No. 61/426,491, filed on Dec. 22, 2010.

(51) Int. Cl.
| | |
|---|---|
| *C07F 11/00* | (2006.01) |
| *C07F 3/06* | (2006.01) |
| *C07F 3/00* | (2006.01) |
| *G01N 21/47* | (2006.01) |
| *C07C 229/76* | (2006.01) |

(52) U.S. Cl.
CPC .......... *C07F 11/005* (2013.01); *C07C 229/76* (2013.01); *C07F 3/003* (2013.01); *C07F 3/06* (2013.01); *G01N 21/4788* (2013.01); *G01N 2021/4769* (2013.01)

(58) Field of Classification Search
CPC .......... C07F 11/005; C07F 3/06; C07F 3/003; G01N 21/4788; G01N 2021/4769; C07C 229/76
See application file for complete search history.

(56) References Cited

U.S. PATENT DOCUMENTS

2011/0118490 A1 * 5/2011 Hwang ................. C07F 11/005
556/44

FOREIGN PATENT DOCUMENTS

EP    2072116 A1    6/2009

OTHER PUBLICATIONS

Xie et al., "Rational Designs of MOFs Constructed from Modified Aromatic Amino Acids," Chem. Eur. J., vol. 13, pp. 9399-9405 (2007).*

Lee et al. "One-Dimensional Double Helical Structure and 4-Fold Type [2+2] Interpentration of Diamondoid Networks with Helical Fashion," Crystal Growth & Design, vol. 8, No. 2, pp. 587-591 (2008).*

(Continued)

*Primary Examiner* — Randy P Gulakowski
*Assistant Examiner* — Ha S Nguyen
(74) *Attorney, Agent, or Firm* — Knobbe, Martens, Olson & Bear, LLP

(57) ABSTRACT

Described herein are multi-dimensional networks that can include a recurring unit of Formula (I) and a recurring unit of Formula (II), and methods of synthesizing and using the same.

39 Claims, 21 Drawing Sheets augmented regular nets augmented quasiregular augmented dual of quasiregular

(56) References Cited

OTHER PUBLICATIONS

Rabone et al. "An Adaptable Peptide-Based Porous Material," Science, vol. 329, Aug. 27, 2010, pp. 1053-1057.*
International Search Report and Written Opinion dated Aug. 22, 2013 for Patent Application No. PCT/US2011/066648, filed Dec. 21, 2011.
Rabone, J. et al. An Adaptable Peptide-Based Porous Material, Science, Aug. 27, 2010, vol. 329, pp. 1053-1057.
Lee, H. Y. et al. Covalent Metal-Peptide Framework Compounds that Extend in One and Two Dimensions, Cryst. Growth & Design, 2008, vol. 8, pp. 296-303.
Smaldone, R. A. et al. Metal-Organic Frameworks from Edible Natural Products, Angew. Chem. Int. Ed. Aug. 16, 2010, vol. 49, pp. 8630-8634.
Mantion, A. et al. Metal-Peptide Frameworks (MPFs): Bioinspired Metal Organic Frameworks, J. Am. Chem. Soc. 2008, vol. 130, pp. 2517-2526.

* cited by examiner

MOSAIC with different functionalities which form the
sequence across the framework

Links

The Links
can have
specific and
sequences
or encoding
(peptides, nucleic
acids, etc.)

Each AA₁ represents an optionally substituted amino acid or an optionally substituted amino acid ester.

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Artificially Synthesized Peptide
<220> FEATURE:
<221> NAME/KEY: VARIANT
<222> LOCATION: 2, 3
<223> OTHER INFORMATION: Xaa = Phe(p-carboxy)

<400> SEQUENCE: 1

Glu Xaa Xaa Ala Gly
1               5
```

MULTI-DIMENSIONAL NETWORKS

CROSS-REFERENCE TO RELATED APPLICATIONS

This application claims the benefit of U.S. Provisional Application No. 61/426,491, filed Dec. 22, 2010, which are incorporated herein by reference in its entirety, including any drawings.

SEQUENCE LISTING

The present application is being filed along with a Sequence Listing in electronic format. The Sequence Listing is provided as a file entitled MIRO003WOSequenceListing.TXT, created Dec. 21, 2011, which is 1 kb in size. The information in the electronic format of the Sequence Listing is incorporated herein by reference in its entirety.

BACKGROUND

Field

The present application relates to the fields of chemistry and material science. More particularly, disclosed herein are multi-dimensional networks that can include a recurring unit of Formula (I) and a recurring unit of Formula (II), and methods for synthesizing the same. Also disclosed herein are methods of utilizing the networks described herein for various uses.

Description

Porous network materials of metal oxides (e.g. zeolites, SBA type materials) and metal-organic frameworks (MOFs) are relatively well known. Typically these materials have regular structures with local or global identical repeating units. MOFs are hybrid materials which consist of an inorganic cluster (determines the topology of the network) and an organic linker, which can be employed in a modular manner and allows pore size and functionality to be designed in a variable manner. MOFs typically comprise one bidentate organic compound coordinated to one metal oxide molecular complex.

Several organometallic complexes have been proposed for the storage of gaseous carbon containing species; however, the complexes previously disclosed are unstable at moderate temperatures and difficult to synthesize. Furthermore, the storage capacity achieved in practice using these materials is low. Functional groups have been added to the linkers of MOFs to impart functionality to the pores as catalysts, however, the bulk materials have been relatively inactive as catalysts with only local functional properties. Further, specific synthetic building blocks have been limited.

SUMMARY

Some embodiments described herein relate to a multi-dimensional network that can include a first recurring unit having the structure of Formula (I); and a second recurring unit having the structure of Formula (II):

$$—[J(A)_n]—$$ (I)

$$—[L]—$$ (II)

wherein: J can be a first group that can include one selected from a metal ion, a carbon atom and an organic-based group; A can be selected from a bond, oxygen, sulfur, phosphorus, selenium and arsenic; n can be an integer ≥3; L can be a second group that comprises at least one selected from an optionally substituted amino acid, an optionally substituted amino acid ester, an optionally substituted peptide, an optionally substituted carbohydrate and an optionally substituted nucleic acid; wherein the number of recurring units of Formula (II) connected to each recurring unit of Formula (I) is equal to n; wherein if A is a bond, the number of recurring units of Formula (II) connected to J is equal to n; and wherein in the recurring unit of Formula (I), the number of A groups attached to each J is equal to n, and each A in the recurring unit of Formula (I) cannot be connected to another A.

Other embodiments described herein relate to methods of making a multi-dimensional network described herein.

Still other embodiments described herein relate to using a network described herein for a variety of uses.

These and other embodiments are described in greater detail below.

DETAILED DESCRIPTION

Figure 1:
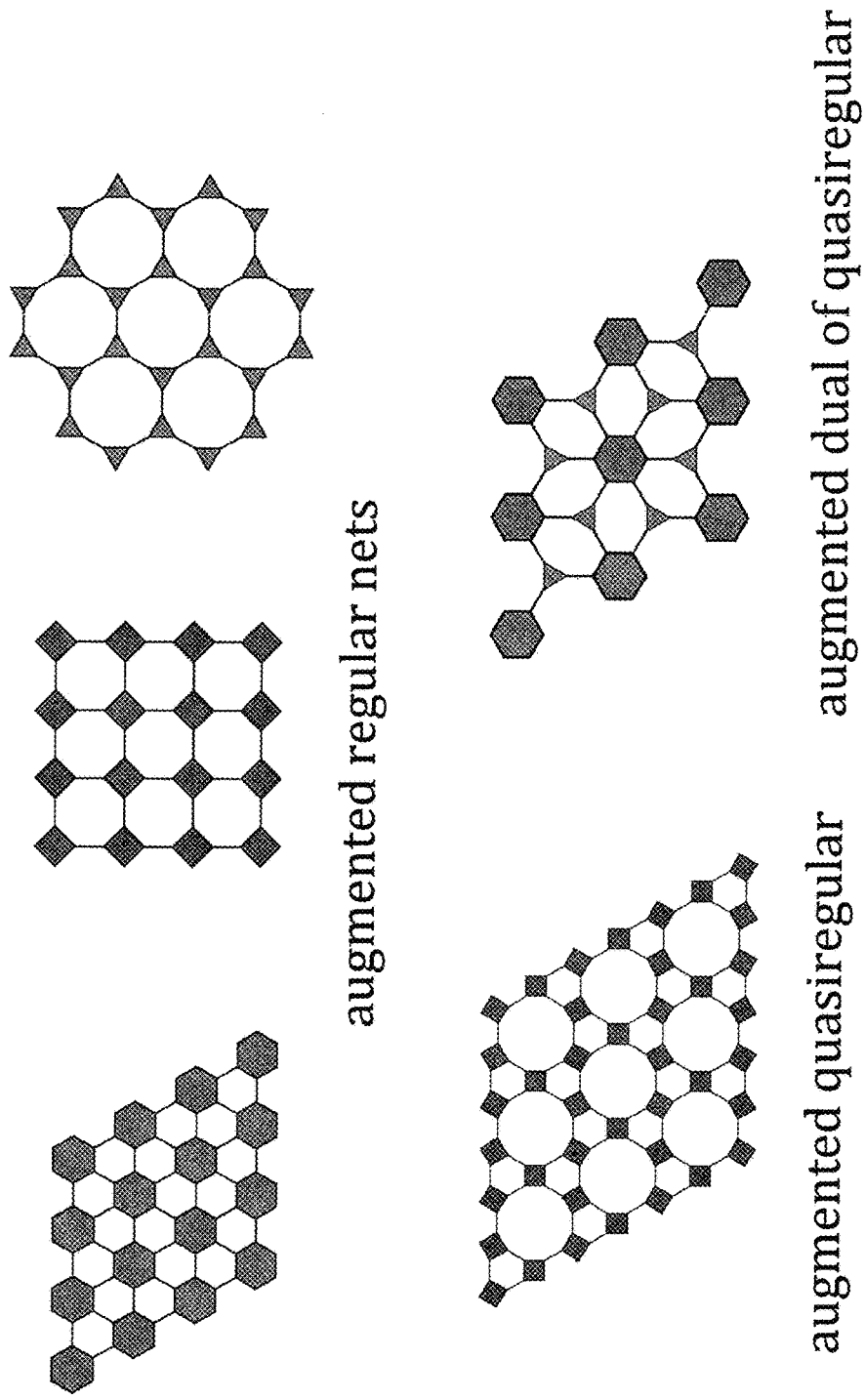
FIG. 1 shows examples of networks.
Figure 1:
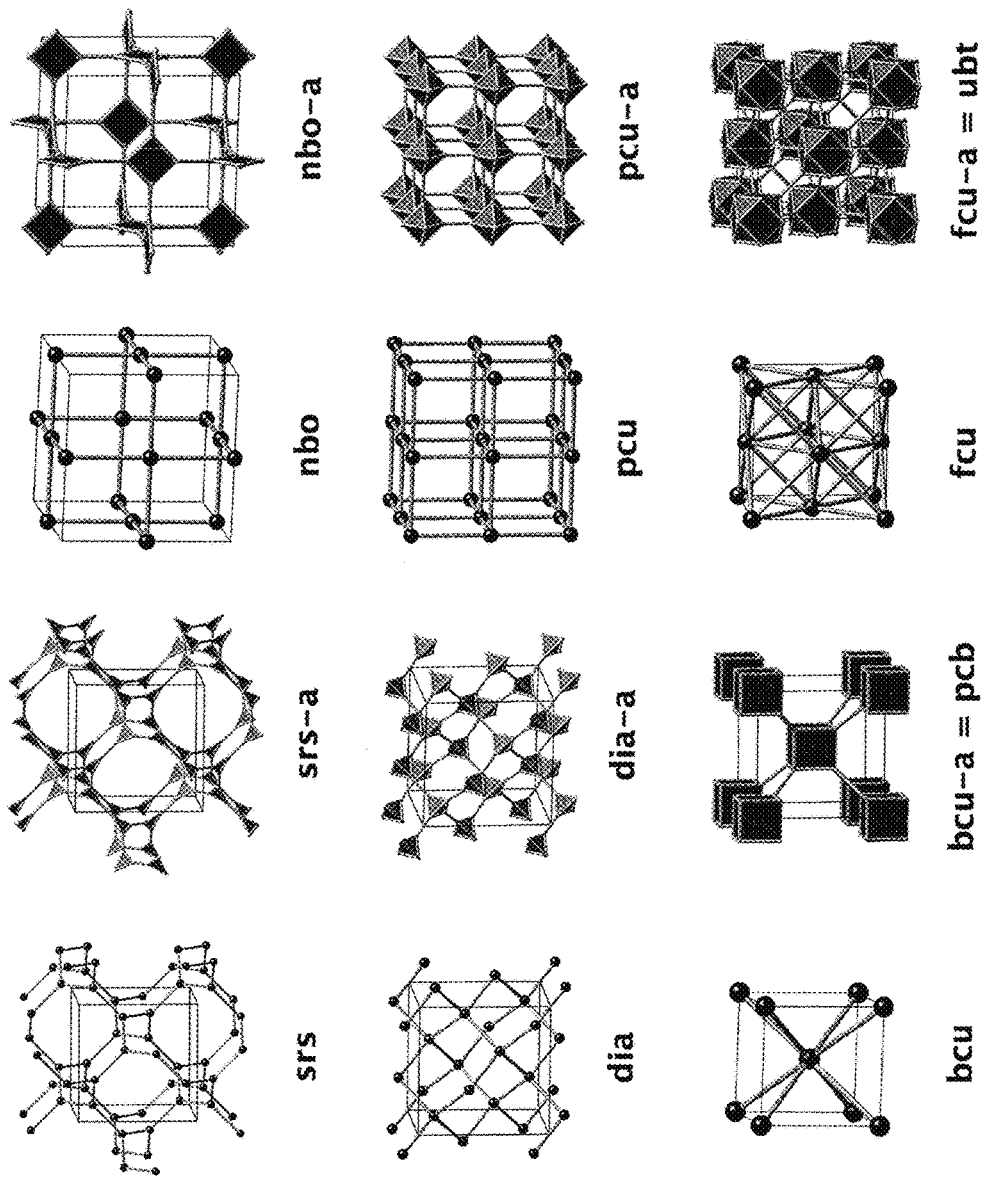
Figure 1:
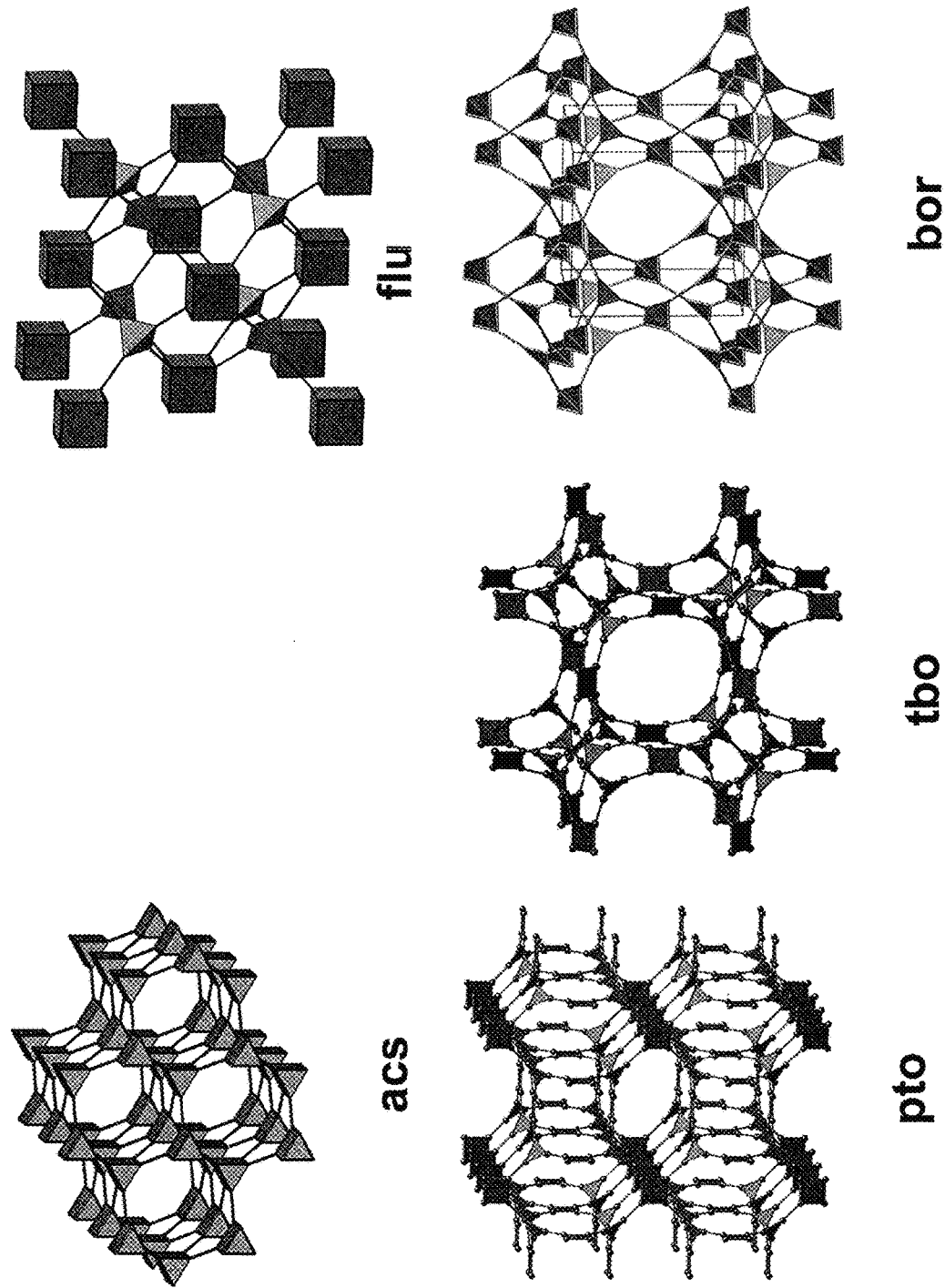
Figure 1:
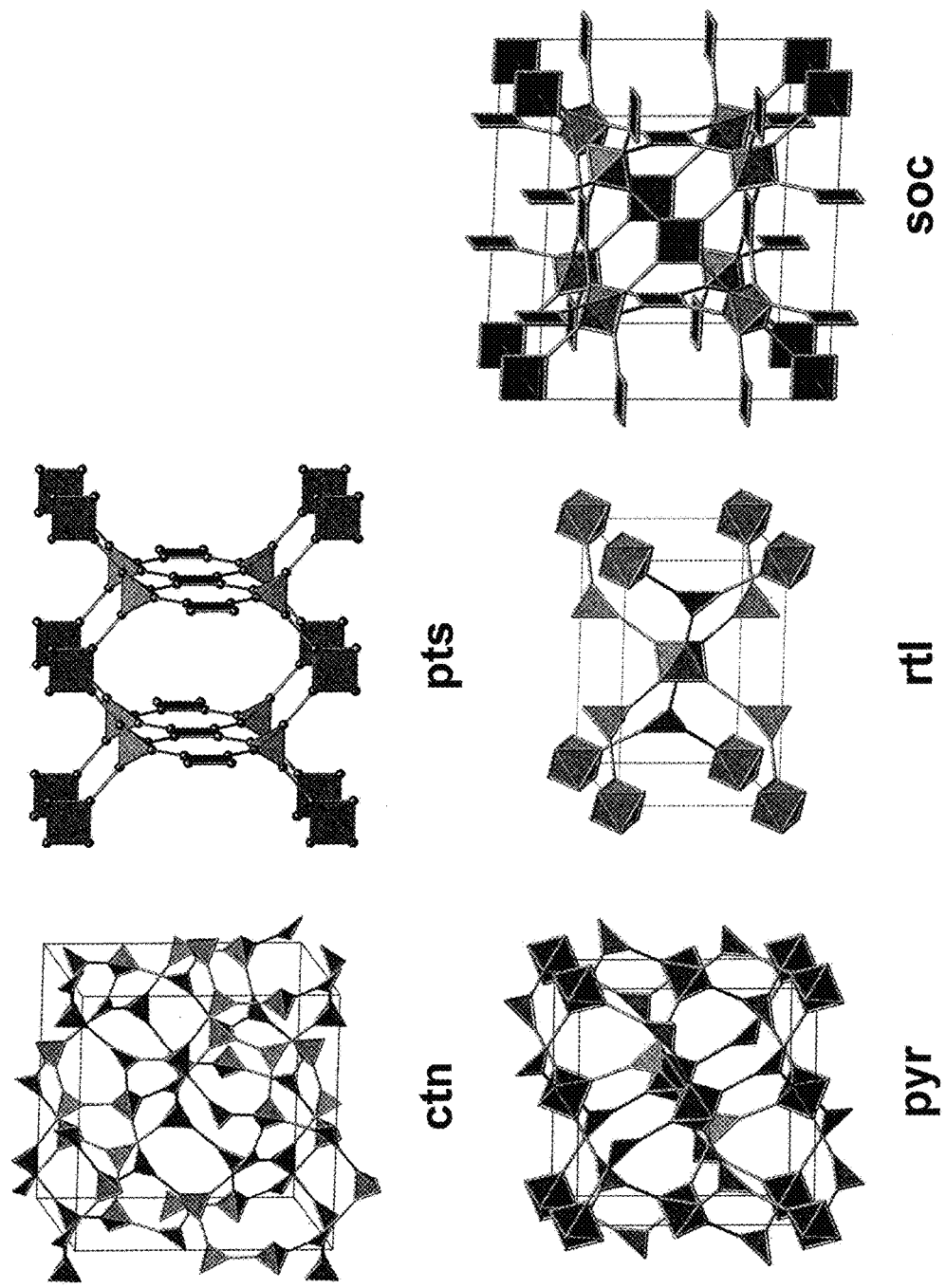
Figure 1:
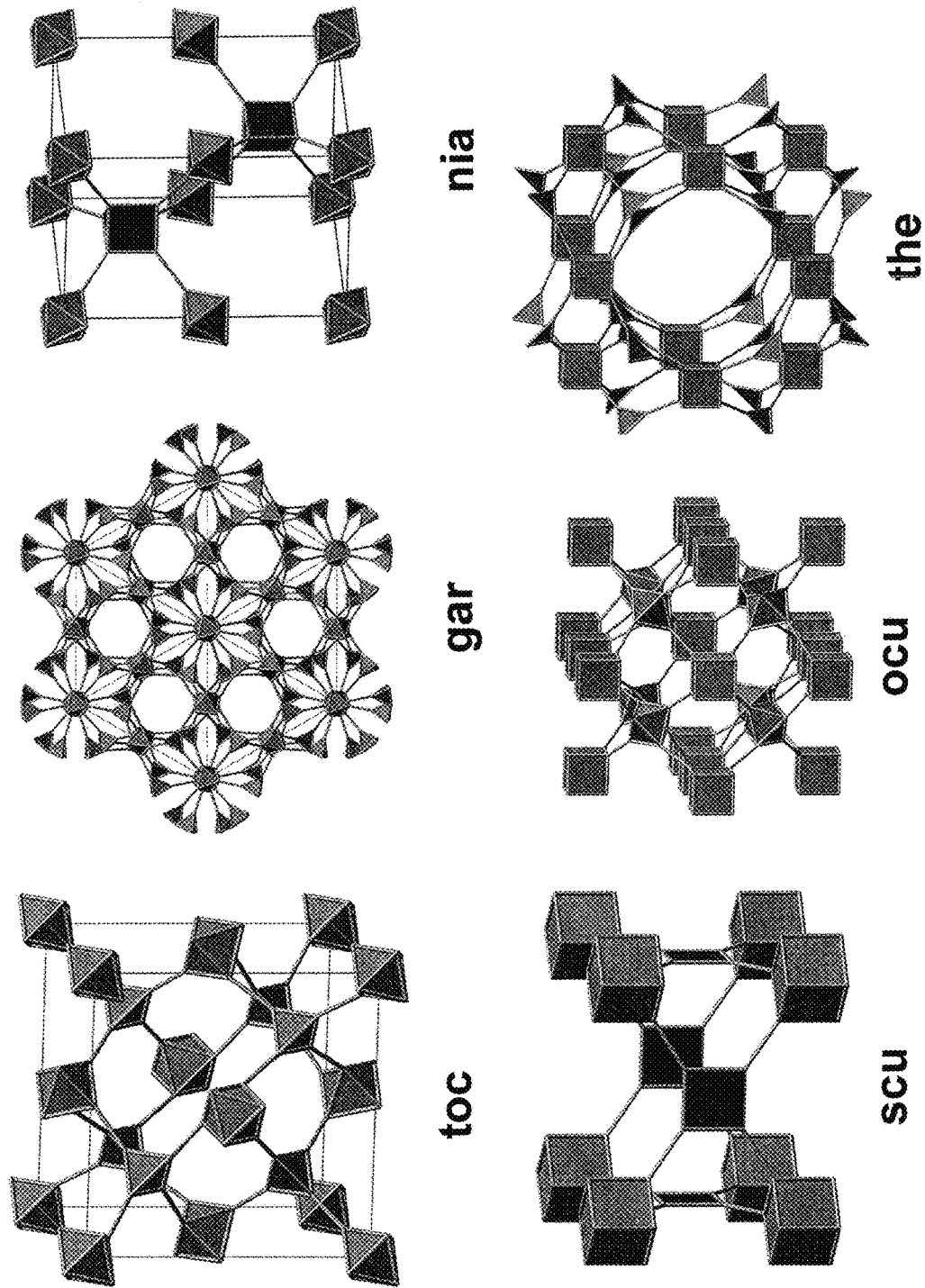
Figure 1:
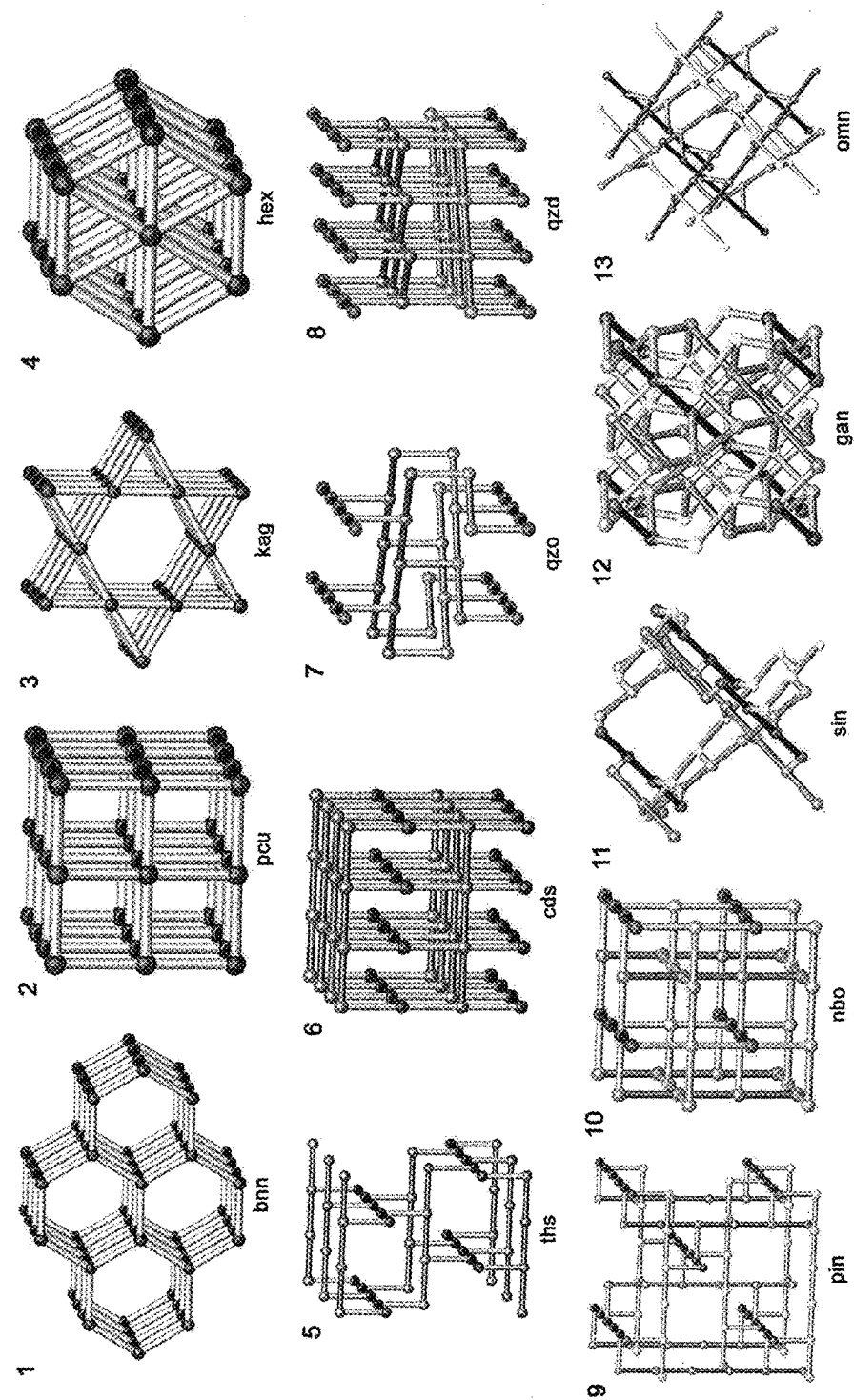
Figure 1:
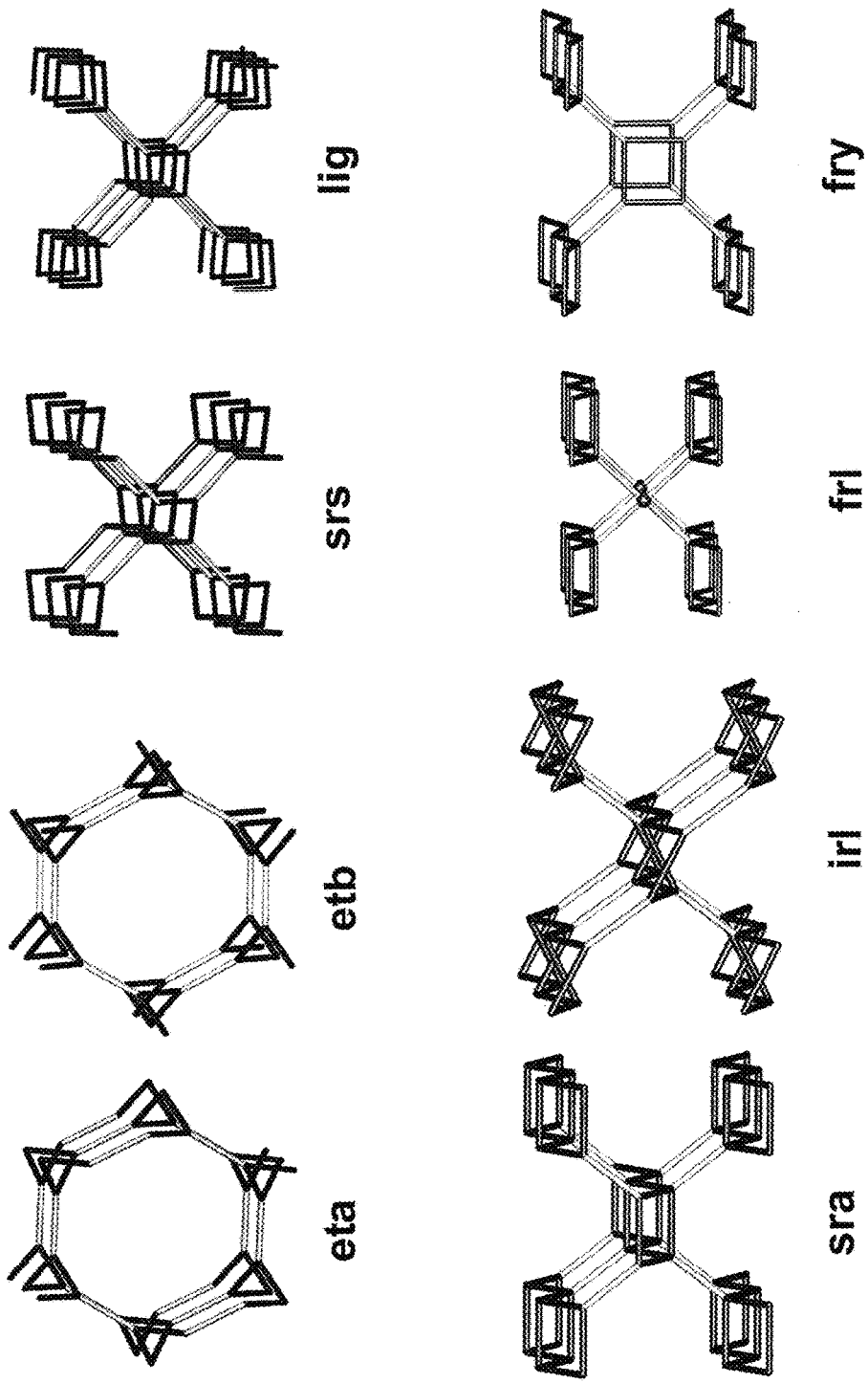

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino and di-substituted amino.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl and the like.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocyclyl may optionally contain one or more unsaturated bonds situated in such a way, however, that a fully delocalized pi-electron system does not occur throughout all the rings. The heteroatoms are independently selected from oxygen, sulfur, and nitrogen. A heterocyclyl may further contain one or more carbonyl or thiocarbonyl functionalities, so as to make the definition include oxo-systems and thio-systems such as lactams, lactones, cyclic imides, cyclic thioimides, cyclic carbamates, and the like. When composed of two or more rings, the rings may be joined together in a fused fashion. Additionally, any nitrogens in a heterocyclyl may be quaternized. Heterocyclyl groups may be unsubstituted or substituted. Examples of heterocyclic groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3, 5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein an "organic-based group" is a chemical group that contains two or more aryls (e.g., biphenyl), two or more heteroaryls and/or two or more heterocycles, each of which can be substituted or unsubstituted. The organic-based group can contain carbon, hydrogen, nitrogen, phosphorous, oxygen, sulfur and/or halogen atoms. For example, the organic-based group can contain two heteroaryl groups linked together by any one or more of the following: an alkylene group (for example, methylene, ethylene and propylene), an amide, an ether and/or a thioether.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine. Amino acids can be substituted or unsubstituted. In some embodiments, the carboxylate portion of the amino acid can be modified to an amido.

The term "amino acid ester" refers to an amino acid in which a carboxylic acid group has been converted to an ester group. In some embodiments, the ester group has a formula selected from alkyl-O—C(=O)—, cycloalkyl-O—C(=O)—, aryl-O—C(=O)— and aryl($C_{1-6}$ alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)—. N-linked amino acid ester can be substituted or unsubstituted.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

The term "pore" as used herein refers to an opening or space within a multi dimensional network (as described herein), having a size that accommodates one or a few relatively small molecules or molecular species. For example, a pore may be an interstitial opening within the framework of an Extensive Mosaic Framework (as described herein).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

As used herein, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

Some embodiments described herein relate to a multi-dimensional network that can include a first recurring unit having the structure of Formula (I); and a second recurring unit having the structure of Formula (II):

$$—[J(A)_n]— \quad (I)$$

$$—[L]— \quad (II)$$

wherein: J can be a first group that can include one selected from a metal ion and an organic-based group; A can be selected from a bond, oxygen, sulfur, phosphorus, selenium and arsenic; n can be an integer ≥3; L can be a second group that comprises at least one selected from an optionally substituted amino acid, an optionally substituted amino acid ester, an optionally substituted peptide, an optionally substituted carbohydrate and an optionally substituted nucleic acid; wherein the number of recurring units of Formula (II) connected to each recurring unit of Formula (I) is equal to n; wherein if A is a bond, the number of recurring units of Formula (II) connected to J is equal to n; and wherein in the recurring unit of Formula (I), the number of A groups attached to each J is equal to n, and each A in the recurring unit of Formula (I) cannot be connected to another A. In some embodiments, the multi-dimensional network can be 0-dimensional. In other embodiments, the multi-dimensional network can be 1-dimensional. In still other embodiments, the multi-dimensional network can be 2-dimensional. In yet still other embodiments, the multi-dimensional network can be 3-dimensional. Examples of network that can be formed are shown in FIG. 1. Additional networks examples of networks can be obtained at http://rcsr.anu.edu.au/, which is hereby incorporated by reference for the specific purpose of providing examples of additional networks.

In some embodiments, the first recurring units of Formula (I) and the second recurring units of Formula (II) can be arranged to form various multi-dimensional networks that have units which form a framework structure with pores. These multi-dimensional structures can be referred to as Extensive Mosaic Frameworks (EMFs). For example, the multi-dimensional network can be comprised of J and A units as shown below, wherein each line between the A's indicate a linker, such as a recurring unit of Formula (II).

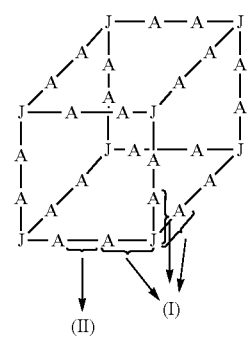

In some embodiments, a joint, as described herein, refers to a recurring unit of Formula (I). A joint can have 3 or more sites for connection. In some embodiments joints can be connected via linkers. In other embodiments joints can be connected to another identical or different joint. A joint can be an inorganic-based joint or an organic-based joint. In some embodiments, the joint can be a carbon atom.

Figure 2:
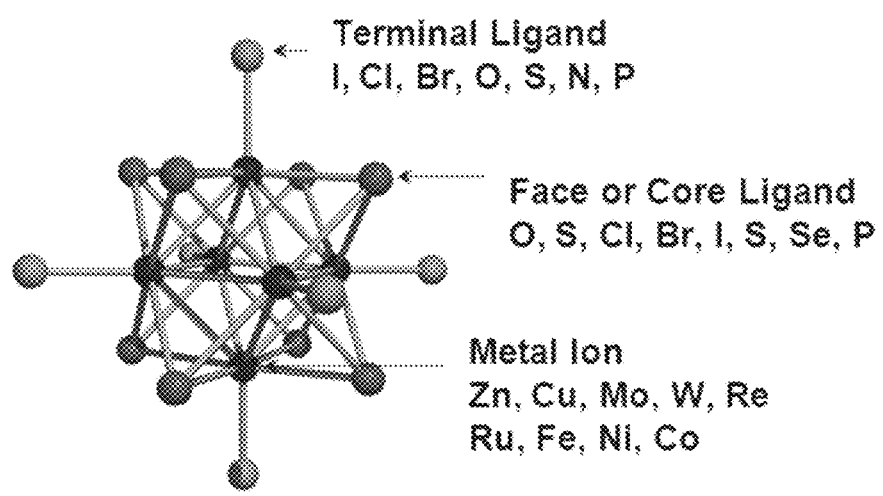
FIG. 2 an example of an inorganic based joint.

An inorganic-based joint includes at least one metal ion that can be coordinated to one or more atoms and/or groups such as oxygen, sulfur, phosphorus, nitrogen, selenium, boron and arsenic. Suitable metal ions are described herein. In some embodiments, an inorganic-based joint can include a metal ion selected from Zn, Cu, Cd and Ca. Examples of inorganic-based joints are generally of the form $(M1_{xm}M2_{ym}Mn_{zm}A1_{xa}A2_{ya}An_{za})T1_{tm1}T2_{tm2}Tn_{tm3}$, wherein M1, M2 and Mn represent different metal ions; A1, A2 and An represent coordinating species, for example, O, S, P, N, Se, As, B and C; T1, T2, and Tn represent terminating ligand species including, but not limited to, O, S, P, N, Se, As, B, C, Br, Cl, I and $CO_2$, xm, ym, zm, xa, ya, za, tm1, tm2 and tm3 can be independently 0 to 100, provided that the sum of xm, ym and zm is greater than or equal to 1, the sum of xa, ya and za is greater than or equal to 1 and the sum of tm1, tm2 and tm3 is greater than or equal to 1; and n is 1 to 10. Examples of inorganic-based joints include, but are not limited to, $Zn_4O(CO_2)_6$, $Cu_2(CO_2)_4Cr_3O(CO_2)_6$, $MnCr_2O_7(CO_2)_6$, $Si_3O_9(CO_2)_6$, $Ba_2Zn_{1-x}Cu_xF_6$, $FeCr_2O_4(CO_2)_6$, $Mo_2O_8Zn_3[(O)_3(CO_2)_3]$, $Fe(OH)(CO_2)_2$, $Al_8(OH)_4(OCH_3)_8$, $Mo_3S_4(BO_3)$, $Cu_4S_6(H)_4$, $Cu_xSe_y(SeC_6H_4SMe)_9(PPh_3)_z$, $Cu_{93}Se_{42}(SeC_6H_4SMe)_9(PPh_3)_{18}$, $Bi_4Cl_{28}$, $S_4N_4Cl_4$, $P_4S_{10}$, $Cu_{30}Fe_2Se_6(SePh)_{24}(dppm)_4$ and $Cu_{26}Se_{13}(PEt_3)_{14}$. FIG. 2 shows an example of an inorganic based joint.

An organic-based joint refers to an "organic-based" group as defined herein. In some embodiments, the multi-dimensional network can have all the joints be the same. In other embodiments, the multi-dimensional network can have two or more different kinds or types of joints. For example, the multi-dimensional network can include two different metal ions. In still other embodiments, the multi-dimensional network can have three, four, or five or more different kinds or types of joints.

Figure 3:
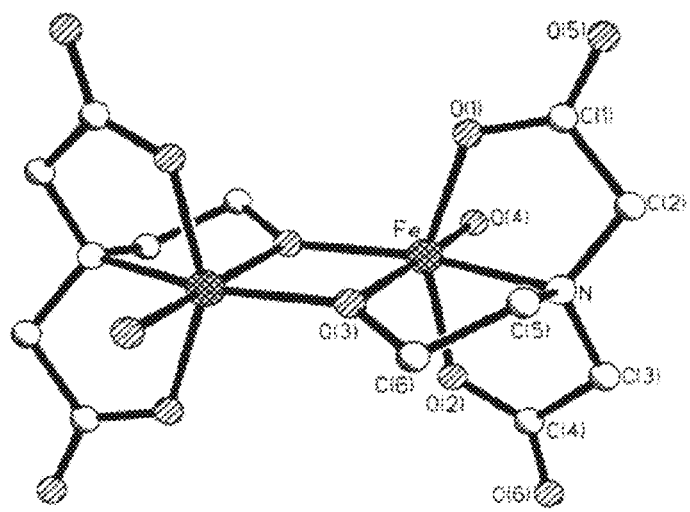
FIG. 3 shows the structure of structure of [Fe(heidi)(H$_2$O)]$_2$.

As discussed herein, in some embodiments the joint contains specific atoms or groups of atoms with properties such that the joint can interact cooperatively with one or more other joints, links and/or species within the material either locally or over more extended distances to impart specific properties to the material. For example, in some embodiments, the joints can include $[Fe(heidi)(H_2O)]_2$, wherein heidi is $[(H3heidi=N(CH_2COOH)_2(CH_2CH_2OH)$. The structure of $[Fe(heidi)(H_2O)]_2$ is shown in FIG. 3. When this joint is used in an extended structure, such as a network described herein, the extended structure material can have magnetic properties due to the cooperative spin interactions of the individual joints, and those properties can be different than the properties of the individual joints alone or their simple sum. In a sensor application, specific analytes introduced into the porous matrix will cause changes in the distance between the specific spin active centers and modulate the magnetic properties. In another example, $Ga_6P_4$, joints in an extended structure can give rise to non-linear optical absorbances due to the cooperative interaction of the optical dipoles of the individual joint clusters. When shaped into a macrostructure that is periodic in 1, 2, or 3 dimensions, the material can have activity as a photonic crystal. The optical properties can be modulated by specific molecules within the matrix allowing the material to be used as a sensor (chemo-optics).

In some embodiments, a link or linker, as described herein, refers to a recurring unit of Formula (II). A link can have only 2 sites for connection. In some embodiments, linkers can connect joints. In other embodiments linkers can be connected to each other. Various groups can be included in a link. In some embodiments, the link can include an optionally substituted amino acid. In other embodiments, the link can include an optionally substituted amino acid ester. In still other embodiments, the link can include an optionally substituted peptide. In yet still other embodiments, the link can include an optionally substituted nucleic acid. In some embodiments, the link can include an optionally substituted carbohydrate. A link can also include various other groups, for example, optionally substituted cycloalkyls, optionally substituted cycloalkenyls, optionally substituted aryls, optionally substituted heteroaryls and/or optionally substituted heterocyclyls. In a multi-dimensional network, all the links can be the same or two, three, four or four or more different kinds or types of links can be included in the network.

A recurring unit of Formula (I) can include a metal ion and/or an organic-based group. Suitable metal ions are known to those skilled in the art. For example, the metal ion can be selected from $Mg^{+2}$, $Ca^{+2}$, $Sr^{+2}$, $Ba^{+2}$, $Sc^{+3}$, $Ti^{+4}$, $Zr^{+4}$, $Hf^{+4}$, $V^{+4}$, $V^{+3}$, $V^{+2}$, $Nb^{+3}$, $Ta^{+3}$, $Cr^{+3}$, $Mo^{+3}$, $W^{+3}$, $Mn^{+3}$, $Mn^{+3}$, $Re^{+3}$, $Re^{+2}$, $Fe^{+3}$, $Fe^{+2}$, $Ru^{+3}$, $Ru^{+2}$, $Os^{+3}$, $Os^{+2}$, $Co^{+3}$, $Co^{+2}$, $Rh^{+2}$, $Rh^{+}$, $Ir^{+2}$, $Ir^{+}$, $Ni^{+2}$, $Pd^{+2}$, $Pd^{+}$, $Pt^{+2}$, $Pt^{+}$, $Cu^{+2}$, $Ag^{+}$, $Au^{+}$, $Zn^{+2}$, $Cd^{+2}$, $Hg^{+2}$, $Al^{+3}$, $Ga^{+3}$, $In^{+3}$, $Tl^{+3}$, $Si^{+4}$, $Si^{+4}$, $Si^{+2}$, $Ge^{+4}$, $Ge^{+4}$, $Ge^{+2}$, $Sn^{+4}$, $Sn^{+2}$, $Pb^{+4}$, $Pb^{+2}$, $As^{+5}$, $As^{+3}$, $As^{+}$, $Sb^{+5}$, $Sb^{+3}$, $Sb^{+}$, $Bi^{+5}$, $Bi^{+3}$ and $Bi^{+}$. In some embodiments, the metal ion can be $Zn^{+2}$. Examples of organic-based groups include, but are not limited to the following,

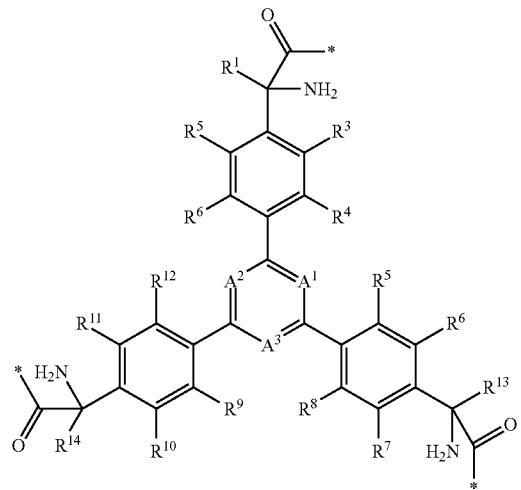

wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ can be independently hydrogen or a substituent described above in the definition of "optionally substituted;" $A^1$, $A^2$ and $A^3$ can be independently nitrogen or CH; and * are points of attachment.

Several recurring units of Formula (I) can be included in the multi-dimensional network. In some embodiments, the recurring units of Formula (I) in the multi-dimensional network can be the same. In other embodiments, the multi-dimensional network can include two different recurring units of Formula (I). For example, the multi-dimensional network can include a plurality of recurring units of Formula (I) that include $Zn^{+2}$ ions and a plurality of recurring units of Formula (I) that include $Cu^{+2}$ ions. In still other embodiments, the multi-dimensional network can include multi different recurring units of Formula (I). In yet still other embodiments, the multi-dimensional network can include four different recurring units of Formula (I). In some embodiments, the multi-dimensional network can include more than four different recurring units of Formula (I).

Various recurring units of Formula (II) can also be included in the multi-dimensional network. In some embodiments, the recurring unit of Formula (II) can include a second group that comprises at least one selected from the group consisting of an optionally substituted amino acid, an optionally substituted amino acid ester, an optionally substituted peptide, an optionally substituted carbohydrate and an optionally substituted nucleic acid. In some embodiments, the recurring unit of Formula (II) can include an optionally substituted amino acid. Various amino acids and amino acid esters can be included in a recurring unit of Formula (II). Those skilled in the art understand that when the amino acid is connected to a recurring unit of Formula (I) through the amino group, one of the hydrogens of the amino group is absent. Similarly, when the amino acid is connected to a recurring unit of Formula (I) through the carboxylic acid, the hydrogen of the carboxylic acid is absent. An example of an amino acid being connected to two recurring units of Formula (I) is shown below.

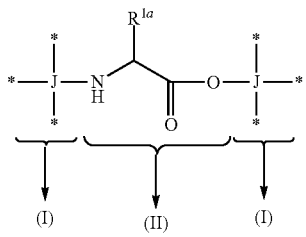

wherein $R^{1a}$ is the pendant portion of the amino acid. For example, $R^{1a}$ is —H (glycine), —CH$_3$ (alanine), —CH$_2$C(=O)NH$_2$ (asparagine), —CH$_2$SH (cysteine), —CH$_2$CH$_2$C(=O)NH$_2$ (glutamine) —CH(CH$_3$)CH$_2$CH$_3$ (isoleucine), —CH$_2$CH(CH$_3$)$_2$ (leucine), —CH$_2$CH$_2$SCH$_3$ (methionine), —CH$_2$-phenyl (phenylalanine), $R^{1a}$ and the carbon to which it is attached are taken together to form a 2-PYrrolidinyl (proline), —CH$_2$OH (serine), —CH(CH$_3$)OH (threonine), —CH$_2$-(2-indolyl) (tryptophan), —CH$_2$-(phenyl para-substituted with OH) (tyrosine), —CH(CH$_3$)$_2$ (valine), —CH$_2$C(=O)OH (aspartic acid), —CH$_2$CH$_2$C(=O)OH (glutamic acid), —CH$_2$CH$_2$CH$_2$NHC(=NH)NH$_2$ (arginine), —CH$_2$-(2-imidazolyl) (histidine) or —CH$_2$CH$_2$CH$_2$CH$_2$NH$_2$ (lysine). In some embodiments, the optionally substituted amino acid or the optionally substituted amino acid ester can be in the L-configuration. In other embodiments, the optionally substituted amino acid or the optionally substituted amino acid ester can be in the D-configuration.

Figure 4:
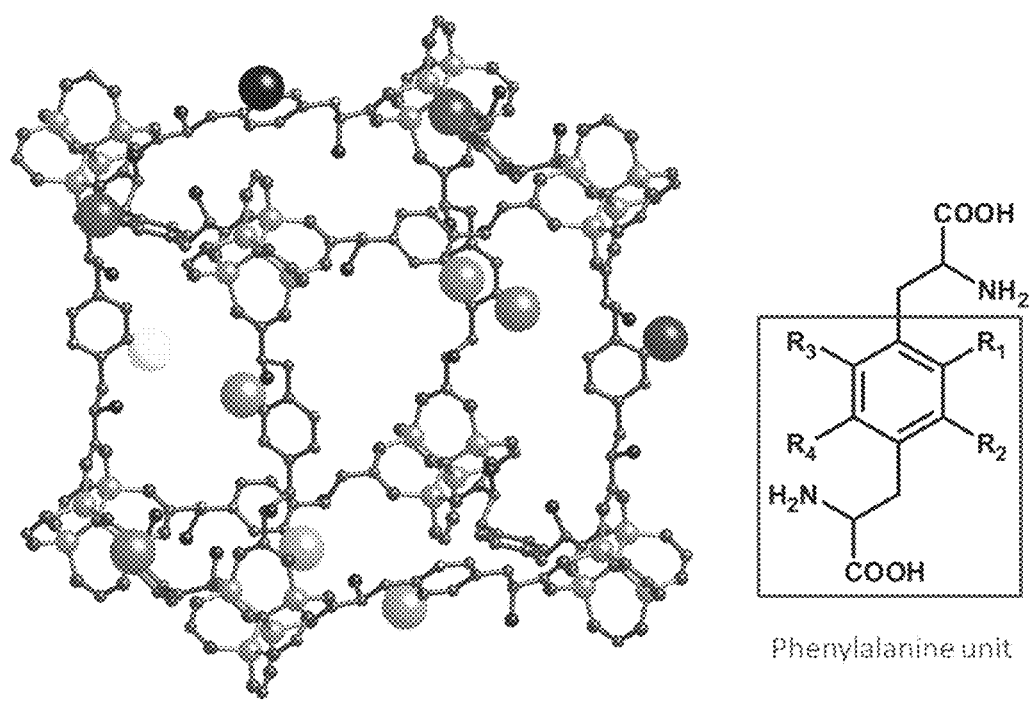
FIG. 4 shows an example of an amino acid based linker.

In some embodiments, L can be an optionally substituted amino acid. An example of an amino acid based linker is shown in FIG. 4. For example, an amino acid that includes 2 carboxylic acid groups can connect to 2 recurring units of Formula (I) (or joint) via the carboxylic acid groups. Those skilled in the art understand that when the carboxylic acid group of an amino acid connects to a recurring unit of Formula (I), the hydrogen atom of the carboxylic acid is no longer present. In some embodiments, L can be

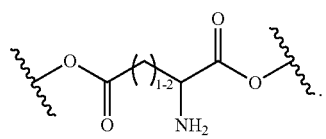

In other embodiments, L can include an optionally substituted amino acid and a second moiety. For example, the second moiety can be selected from an optionally substituted cycloalkyl, an optionally substituted cycloalkenyl, an optionally substituted aryl, an optionally substituted heteroaryl and an optionally substituted heterocyclyl. In some embodiments, L can be a substituted amino acid substituted with a carboxylate group. For example, L can be phenylalanine substituted with a carboxylate group. In some embodiments, L can be

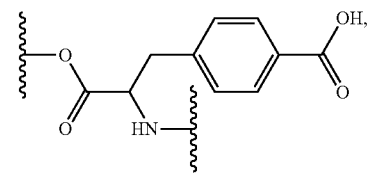 [SMILES: *NC(Cc1ccc(C(=O)O)cc1)C(=O)O*]

or salt thereof. In some embodiments, the —NH and —OC(=O) of an optionally substituted amino acid can be coupled to a recurring unit of Formula (I) (or joint), such that the optionally substituted amino acid acts as a dichelating ligand.

In some embodiments, the amino group of an amino acid can be converted to a carboxylate using methods known to those skilled in the art. The amino acid with two carboxylate groups, in which one is from an amino group that has been converted to an carboxylate, can be connected via the two carboxylate groups. In other embodiments, two or more amino acids can be connected to each other, and the resulting linker can be coordinated to a recurring unit of Formula (I) (or joint) via the free carboxylate groups. In some embodiments, L can include two amino acids coupled together. For example, L can have the structure:

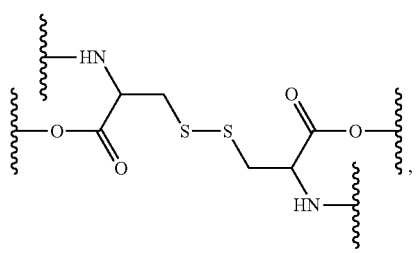

wherein each amino acid acts as a dichelating ligand that can conjugate to a recurring unit of Formula (I). In other embodiments, L can have the structure:

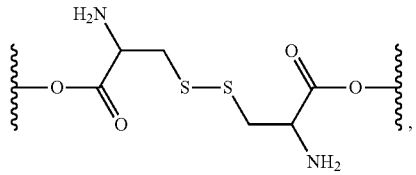

wherein each amino acid acts as a monochelating ligand to a recurring unit of Formula (I).

When L includes an optionally substituted peptide, the peptide can be of various lengths. In some embodiments, the optionally substituted peptide can include 2 to 20 amino acids. In other embodiments, the optionally substituted peptide can include 2 to 10 amino acids. In still other embodiments, the optionally substituted peptide can include 2 to 5 amino acids. The amino acids in the optionally substituted peptide can be the same or different. For example, the optionally substituted peptide can include 2, 3, 4, 5 or more than 5 different amino acids. As understood by those skilled in the art, an optionally substituted peptide can include amide bonds from the reaction of a carboxylic acid group of one amino acid with an amino group of a second amino acid. In some embodiments, L can have the structure

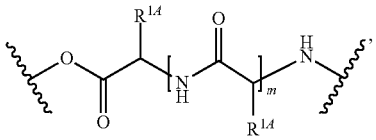

wherein $R^{1A}$ is the pendant portion of the amino acid. For example, $R^{1a}$ is —H (glycine), —CH$_3$ (alanine), —CH$_2$C(=O)NH$_2$ (asparagine), —CH$_2$SH (cysteine), —CH$_2$CH$_2$C(=O)NH$_2$ (glutamine) —CH(CH$_3$)CH$_2$CH$_3$ (isoleucine), —CH$_2$CH(CH$_3$)$_2$ (leucine), —CH$_2$CH$_2$SCH$_3$ (methionine), —CH$_2$-phenyl (phenylalanine), $R^{1a}$ and the carbon to which it is attached are taken together to form a 2-pyrrolidinyl (proline), —CH$_2$OH (serine), —CH(CH$_3$)OH (threonine), —CH$_2$-(2-indolyl) (tryptophan), —CH$_2$-(phenyl para-substituted with OH) (tyrosine), —CH(CH$_3$)$_2$ (valine), —CH$_2$C(=O)OH (aspartic acid), —CH$_2$CH$_2$C(=O)OH (glutamic acid), —CH$_2$CH$_2$CH$_2$NHC(=NH)NH$_2$ (arginine), —CH$_2$(2-imidazolyl) (histidine) or CH$_2$CH$_2$CH$_2$CH$_2$NH$_2$ (lysine); and m can be 2, 3 or 4.

In some embodiments, L can include one or more optionally substituted amino acids and/or one or more optionally substituted amino acid esters. In other embodiments, L can include one or more optionally substituted amino acids and a second moiety. In other embodiments, L can include one or more optionally substituted amino acids, a second moiety and a third moiety. Examples of suitable second and third moieties include an optionally substituted cycloalkyl, an optionally substituted cycloalkenyl, an optionally substituted aryl, an optionally substituted heteroaryl or an optionally substituted heterocyclyl. For example, L can include one or more optionally substituted amino acids and one or more optionally substituted aryls. In some embodiments, the second moiety can be a phenyl substituted with a carboxylate group. In some embodiments, the third moiety can be a phenyl substituted with a carboxylate group. In some embodiments, L can have the structure

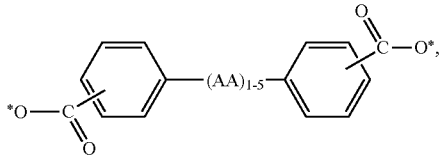

wherein AA represents an optionally substituted amino acid, and wherein the amino acid is coupled to the first phenyl group via a NH and the amino acid is coupled to the second phenyl moiety via a carboxylate group. In some embodiments, L can have the structure

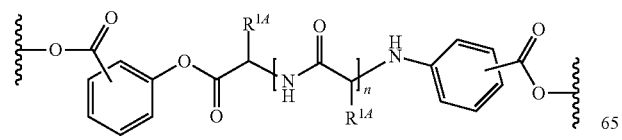

wherein $R^{1A}$ is the pendant portion of the amino acid. For example, $R^{1a}$ is —H (glycine), —CH$_3$ (alanine), —CH$_2$C(=O)NH$_2$ (asparagine), —CH$_2$SH (cysteine), —CH$_2$CH$_2$C(=O)NH$_2$ (glutamine) —CH(CH$_3$)CH$_2$CH$_3$ (isoleucine), —CH$_2$CH(CH$_3$)$_2$ (leucine), —CH$_2$CH$_2$SCH$_3$ (methionine), —CH$_2$-phenyl (phenylalanine), $R^{1a}$ and the carbon to which it is attached are taken together to form a 2-pyrrolidinyl (proline), —CH$_2$OH (serine), —CH(CH$_3$)OH (threonine), —CH$_2$-(2-indolyl) (tryptophan), —CH$_2$-(phenyl para-substituted with OH) (tyrosine), —CH(CH$_3$)$_2$ (valine), —CH$_2$C(=O)OH (aspartic acid), —CH$_2$CH$_2$C(=O)OH (glutamic acid), —CH$_2$CH$_2$CH$_2$NHC(=NH)NH$_2$ (arginine), —CH$_2$(2-imidazolyl) (histidine) or —CH$_2$CH$_2$CH$_2$CH$_2$NH$_2$ (lysine); and n can be 2, 3 or 4. In some embodiments, L can have the structure

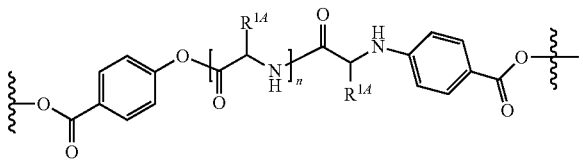

wherein $R^{1A}$ is the pendant portion of the amino acid. For example, $R^{1a}$ is —H (glycine), —CH$_3$ (alanine), —CH$_2$C(=O)NH$_2$ (asparagine), —CH$_2$SH (cysteine), —CH$_2$CH$_2$C(=O)NH$_2$ (glutamine) —CH(CH$_3$)CH$_2$CH$_3$ (isoleucine), —CH$_2$CH(CH$_3$)$_2$ (leucine), —CH$_2$CH$_2$SCH$_3$ (methionine), —CH$_2$-phenyl (phenylalanine), $R^{1a}$ and the carbon to which it is attached are taken together to form a 2-pyrrolidinyl (proline), —CH$_2$OH (serine), —CH(CH$_3$)OH (threonine), —CH$_2$-(2-indolyl) (tryptophan), —CH$_2$-(phenyl para-substituted with OH) (tyrosine), —CH(CH$_3$)$_2$ (valine), —CH$_2$C(=O)OH (aspartic acid), —CH$_2$CH$_2$C(=O)OH (glutamic acid), —CH$_2$CH$_2$CH$_2$NHC(=NH)NH$_2$ (arginine), —CH$_2$(2-imidazolyl) (histidine) or —CH$_2$CH$_2$CH$_2$CH$_2$NH$_2$ (lysine); and n can be 2, 3 or 4. In some embodiments, L can be selected from

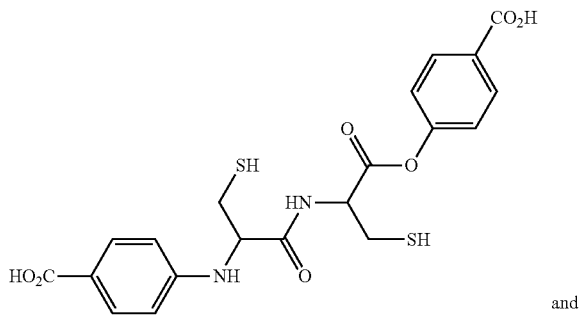

and

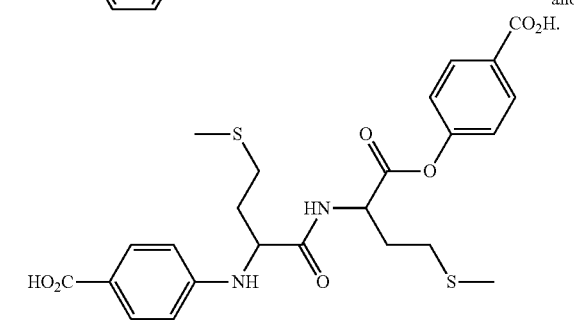

In some embodiments, L can include one or more amino acids in combination with a metal ion. In other embodiments, L can include one or more amino acid esters in combination with a metal ion. Suitable metal ions are described herein. In some embodiments, each amino acid can be a dichelating ligand to the metal ion and include another carboxylate group. In some embodiments, L can have one of the following structures:

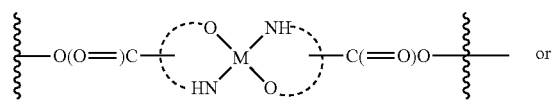

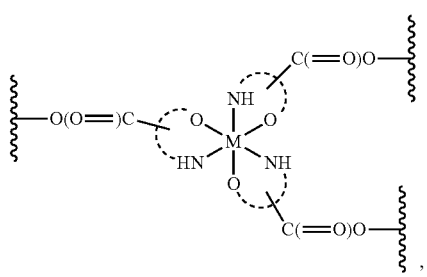

wherein

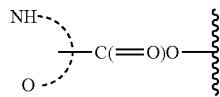

represents an amino acid that includes another carboxylate group that can attach to a recurring unit of Formula (I) (or joint). In some embodiments, the metal ion can be bonded to 2, 3, 4 or more than 4 amino acids.

In other embodiments, the optionally substituted amino acid or the optionally substituted amino ester is not attached to a recurring unit of Formula (I), but is a side chain of a linker, for example a recurring unit of Formula (II). For example, L can be a cycloalkyl, a cycloalkenyl, an aryl, a heteroaryl or a heterocyclyl substituted with two or more carboxylate groups and substituted with an amino acid and/or amino acid ester. In some embodiments, L can have the structure:

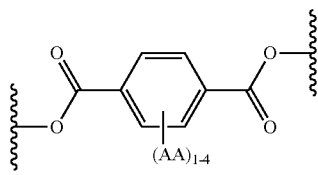

wherein AA represents an amino acid or amino acid ester. In some embodiments, L can be

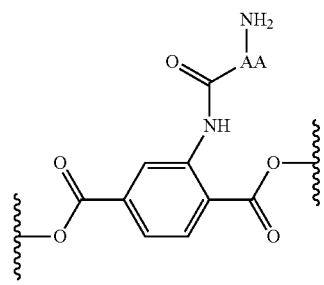

wherein AA represents an amino acid or amino acid ester in which the —NH—C(=O)O is from the carboxylic acid of the amino acid and $NH_2$ is the amino group of the amino acid. In some embodiments, L can be

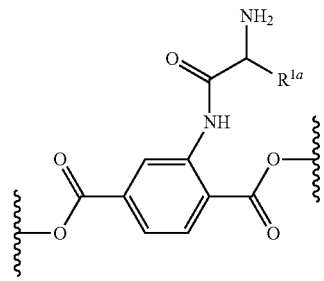

wherein $R^{1A}$ is the pendant portion of the amino acid. For example, $R^{1a}$ is —H (glycine), —$CH_3$ (alanine), —$CH_2C$(=O)$NH_2$ (asparagine), —$CH_2SH$ (cysteine), —$CH_2CH_2C$(=O)$NH_2$ (glutamine) —CH($CH_3$)$CH_2CH_3$ (isoleucine), —$CH_2CH(CH_3)_2$ (leucine), —$CH_2CH_2SCH_3$ (methionine), —$CH_2$-phenyl (phenylalanine), $R^{1a}$ and the carbon to which it is attached are taken together to form a 2-pyrrolidinyl (proline), —$CH_2OH$ (serine), —CH($CH_3$)OH (threonine), —$CH_2$-(2-indolyl) (tryptophan), —$CH_2$-phenyl para-substituted with OH) (tyrosine), —CH($CH_3$)$_2$ (valine), —$CH_2C$(=O)OH (aspartic acid), —$CH_2CH_2C$(=O)OH (glutamic acid), —$CH_2CH_2CH_2NHC$(=NH)$NH_2$ (arginine), —$CH_2$(2-imidazolyl) (histidine) or —$CH_2CH_2CH_2CH_2NH_2$ (lysine). In some embodiments, L can have one of the following structures:

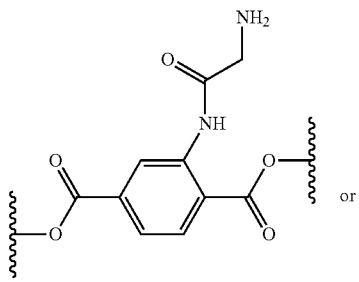 or

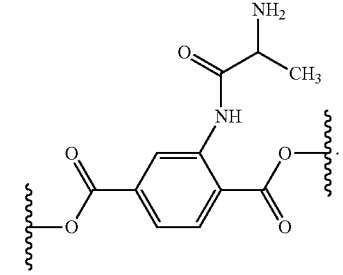

When the carbon to which $R^{1a}$ is attached is a chiral, in some embodiments, the carbon can be an (R)-stereocenter. In other embodiments, carbon to which $R^{1a}$ is attached can be a (S)-stereocenter.

When a recurring unit of Formula (II) includes an optionally substituted amino acid or amino acid ester, a portion of the amino acid or amino acid ester can extend into a pore of the network For example, $R^{1a}$ in the following structure can extend into a pore of the network.

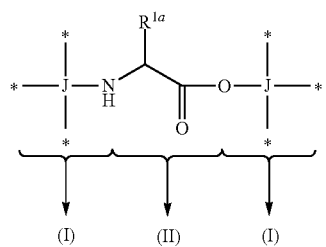

wherein $R^{1A}$ is the pendant portion of the amino acid. For example, $R^{1a}$ is —H (glycine), —CH$_3$ (alanine), —CH$_2$C(=O)NH$_2$ (asparagine), —CH$_2$SH (cysteine), —CH$_2$CH$_2$C(=O)NH$_2$ (glutamine) —CH(CH$_3$)CH$_2$CH$_3$ (isoleucine), —CH$_2$CH(CH$_3$)$_2$ (leucine), —CH$_2$CH$_2$SCH$_3$ (methionine), —CH$_2$-phenyl (phenylalanine), $R^{1a}$ and the carbon to which it is attached are taken together to form a 2-PYrrolidinyl (proline), —CH$_2$OH (serine), —CH(CH$_3$)OH (threonine), —CH$_2$-(2-indolyl) (tryptophan), —CH$_2$-(phenyl para-substituted with OH) (tyrosine), —CH(CH$_3$)$_2$ (valine), —CH$_2$C(=O)OH (aspartic acid), —CH$_2$CH$_2$C(=O)OH (glutamic acid), —CH$_2$CH$_2$CH$_2$NHC(=NH)NH$_2$ (arginine), —CH$_2$(2-imidazolyl) (histidine) or CH$_2$CH$_2$CH$_2$CH$_2$NH$_2$ (lysine).

Figure 9:
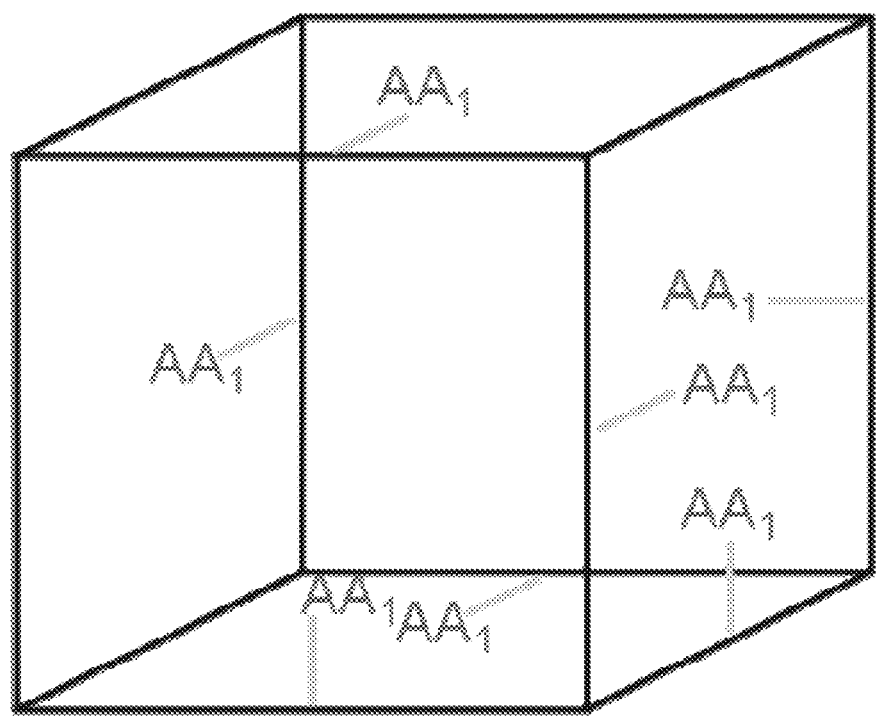
FIG. 9 shows an example of a multi-dimension network having a portion of an optionally substituted amino acid or an optionally substituted amino acid ester extending into a pore of the multi-dimensional network.

In some embodiments, a portion of an optionally substituted amino acid or an optionally substituted amino acid ester can extend into a pore of the multi-dimensional network. In some embodiments, a recurring unit of Formula (II) can include one or more amino acids or one or more amino acid esters in combination with a metal ion, wherein a portion of one or more of the amino acids extends into one or more pores of the multi-dimensional network. In some embodiments, wherein the optionally substituted amino acid is not attached to a recurring unit of Formula (I), but is a side chain of a recurring unit of Formula (II), a portion of the optionally substituted amino acid can extend into one or mores pores of the multi-dimensional network. In some embodiments, when a recurring unit of Formula (II) includes an optionally substituted peptide, a portion of one or more of the amino acids of the peptide can extend into one or more pores of the multi-dimensional network. In some embodiments, when a recurring unit of Formula (II) is an optionally substituted amino acid, a portion of the amino acid can extend into one or more pores of the multi-dimensional network. An example of a multi-dimensional network having a portion of an optionally substituted amino acid or an optionally substituted amino acid ester that can extend into one pore of the multi-dimensional network is shown in FIG. 9.

In some embodiments, a portion of an optionally substituted amino acid or an optionally substituted amino acid ester can extend into one pore of the multi-dimensional network. In other embodiments, a portion of an optionally substituted amino acid or an optionally substituted amino acid ester can extend into two pores of the multi-dimensional network. In yet other embodiments, a portion of an optionally substituted amino acid and/or an optionally substituted amino acid ester can extend into more than two pores of the multi-dimensional network. In some embodiments, the portion of the amino acid extending into a pore(s) can include an amino group. In some embodiments, a pore that includes a portion of an optionally substituted amino acid and/or an optionally substituted amino acid ester can reduce the pore size by at least 5%, at least 10%, at least 25%, at least 35%, at least 50%, at least 60% or at least 75%, when compared to the pore size without the portion of an optionally substituted amino acid and/or an optionally substituted amino acid ester.

By reducing one or more pores in a multi-dimensional network, the pores that are reduced in size can have a higher affinity for a metal ion compared a pore that does not include a portion of an optionally substituted amino acid and/or an optionally substituted amino acid ester. Thus, the size of a pore can be varied to have a higher affinity for an organic molecule, an inorganic moiety (for example, a metal-based catalyst or metal ion), an oligomer or protein, as compared to a pore that does not include a portion of an optionally substituted amino acid and/or an optionally substituted amino acid ester. In some embodiments, the pore of reduced size can have at least 5%, at least 10%, at least 25%, at least 35%, at least 50%, at least 60% or at least 75% higher affinity for an organic molecule, an inorganic moiety (for example, a metal-based catalyst or metal ion), an oligomer or protein. In some embodiments, by having one or more amino groups of an optionally substituted amino acid and/or an optionally substituted amino acid ester, the multi-dimensional network can be used to capture and/or store a gas, such as carbon dioxide. In some embodiments, by having one or more amino groups of an optionally substituted amino acid and/or an optionally substituted amino acid ester, the multi-dimensional network can act as a proton conductor. In some embodiments, when the multi-dimensional network acts as a proton conductor, the multi-conductor can be used in a fuel cell.

As described herein, a recurring of Formula (II) can include an optionally substituted nucleic acid. In some embodiments, the optionally substituted nucleic acid can be connected via an oxygen atom of its phosphate. In other embodiments, the optionally substituted nucleic acid can be connected via the oxygen atom attached to the 5'-carbon. In still other embodiments, the hydroxy group attached to the 5'-carbon can be converted to a carboxylate group, and the optionally substituted nucleic acid can be connected via the carboxylate groups.

A variety of other moieties can be included in a recurring unit of Formula (II). In some embodiments, the recurring unit of Formula (II) can include a third moiety. A non-limiting list of groups that can be a third moiety and be included in a recurring unit of Formula (II) include, but are not limited to, optionally substituted aryls, optionally substituted heteroaryls, optionally substituted heterocycles, optionally substituted cycloalkyls and optionally substituted cycloalkenyls. In some embodiments, the third moiety can be an aryl, for example phenyl, substituted with one or more carboxylic acids and/or one or more carboxylates.

In some embodiments, the recurring units of Formula (II) in the multi-dimensional network can be the same. In other embodiments, the multi-dimensional network can include two different recurring units of Formula (II). In still other embodiments, the multi-dimensional network can include three different recurring units of Formula (II). In yet still other embodiments, the multi-dimensional network can include four different recurring units of Formula (II). In some embodiments, the multi-dimensional network can include more than four different recurring units of Formula (II).

In some embodiments, multi-dimensional network can include recurring units of Formula (II) and linkers that are not recurring units of Formula (II). For example, the multi-dimensional network can include recurring units of Formula (II) and phenyl groups substituted with at least two or more carboxylate groups, wherein the phenyl groups substituted with at least two or more carboxylate groups are also linkers in the multi-dimensional network.

Examples of networks are illustrated schematically below. Structure (A) shows a portion of a network that has the same recurring units of Formula (I) and the same recurring units of Formula (II), Structure (B) shows a portion of a network that has two different recurring units of Formula (I) and the same recurring units of Formula (II), Structure (C) shows a portion of a network that has the same recurring units of Formula (I) and two different recurring units of Formula (II), and Structure (D) shows a portion of a network that has two different recurring units of Formula (I) and two different recurring units of Formula (II).

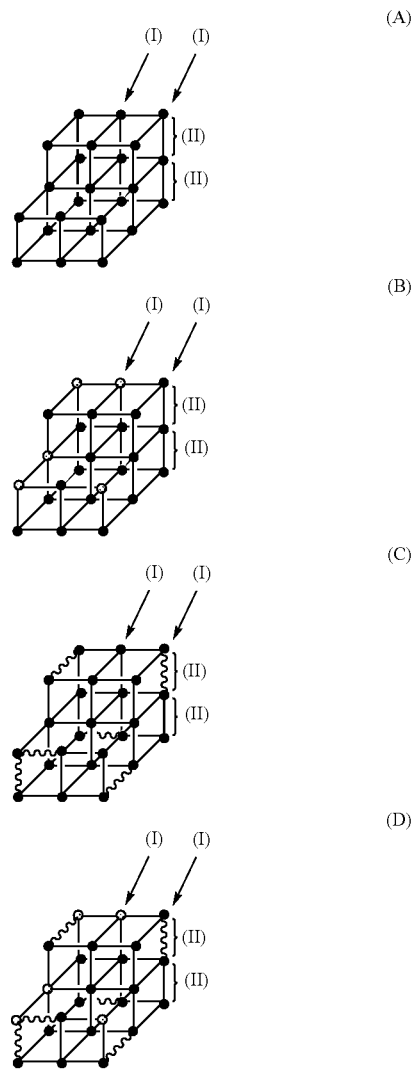

In some embodiments, the multi-dimensional network can be doped with a moiety. For example, the network can be doped with a metal ion, such as those described herein. In other embodiments, the network can be doped with an optionally substituted peptide, an optionally substituted carbohydrate and/or an optionally substituted nucleic acid.

In some embodiments, a linker and/or a recurring unit of Formula (II) can include one or more substituents not attached to recurring unit of Formula (I) or joint, respectively, and the substituent(s) can affect the size of a pore in the network. For example, a linker and/or a recurring unit of Formula (II) can include a moiety that extends into one or more of the interstitial openings or pores of the network. Additionally, in some embodiments, a substituent of one recurring unit of Formula (II) can interact cooperatively with another substituent of another recurring unit of Formula (II) and/or can interact cooperatively with one or more moieties doped into the network, e.g., occupying pores within the network. In some embodiments, the joints can interact cooperatively with one or more other joints. In some embodiments, the linkers can interact cooperatively with one or more other linkers. In some embodiments, one or more joints can interact cooperatively with one or more linkers. The interactions of the substituents, joints, linkers, recurring units of Formula (I) and/or recurring units of Formula (II) may influence one or more properties of the network, such as an electrical, chemical, optical, magnetic and/or physical property. The interactions may be between adjacent units or may be across several units of the network. In some embodiments, one or more properties of the network can be influenced by an outside source, such as a electrical, magnetic and/or electromagnetic field.

Figure 5:
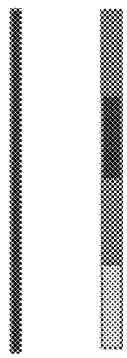
FIG. 5 shows pictorially a multi-dimensional framework that includes specific sequences.
Figure 5:
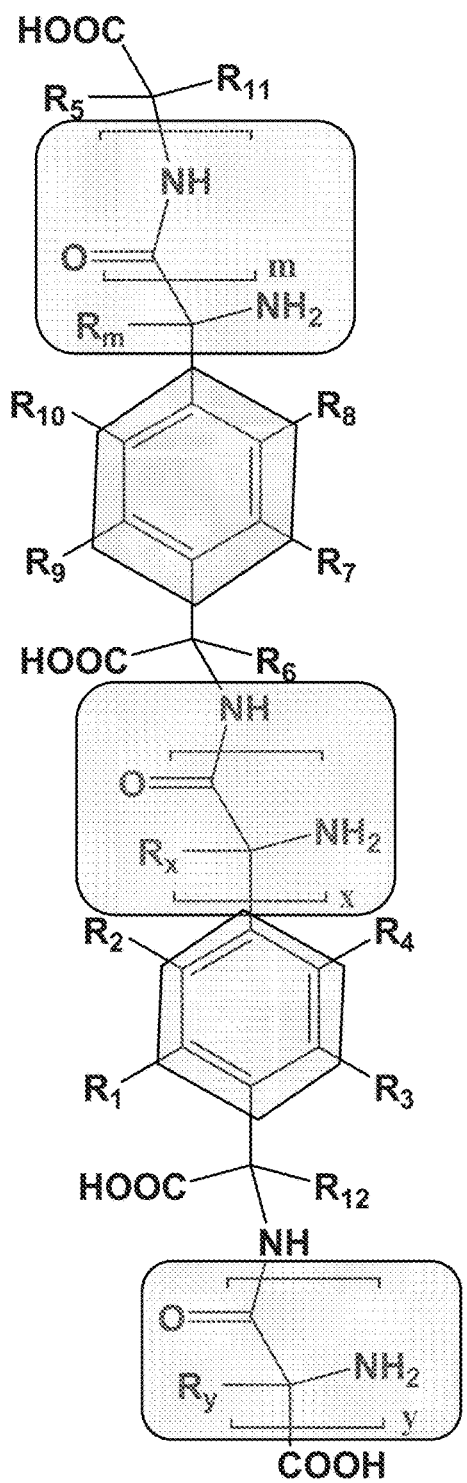

In some embodiments, the multi-dimensional framework can be comprised of specific sequences (for example, specific sequences of peptides and/or nucleic acids) that can be used for encoding. As used herein "encoding" refers to the process of selectively incorporating particular groups in particular arrangements such that the combination of groups and arrangements store information in a manner that can be accessible and/or impart a particular property to the material (for example, the network). For example, a multi-dimensional framework that includes a specific sequence of nucleic acids can be used to produce specific polypeptides. In some embodiments, a multi-dimensional framework can include a specific polypeptide that can function as a transcription vector. An example of a multi-dimensional framework that includes specific sequences is shown pictorially in FIG. 5.

In other embodiments, a network described herewith can have a regular or random or fractal configuration that can be created by virtue of the specific linkers and/or joints selected such that the collective arrangement provides additional functionality. In some embodiments, functionality (for example, porosity) can vary between layers.

Figure 6:
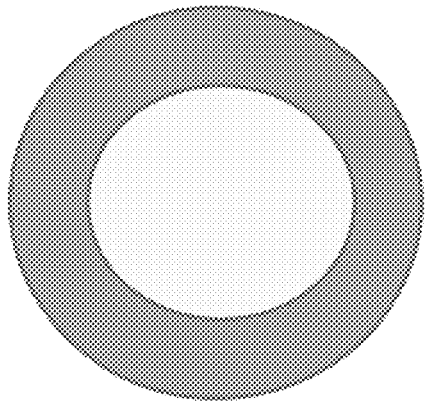
FIG. 6 shows pictorially examples of networks with variable functionality (for example, porosity) and/or structure (for example, one network contained within another network or a non-network material).
Figure 6:
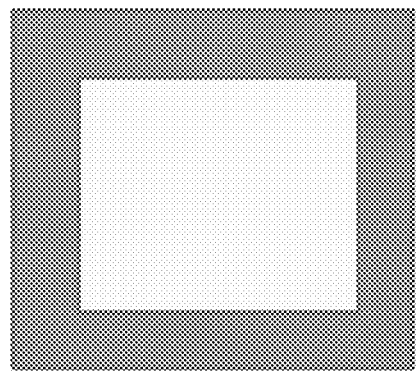
Figure 6:
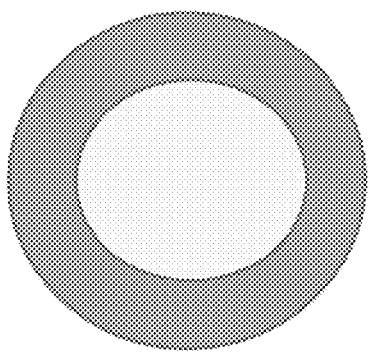
Figure 6:
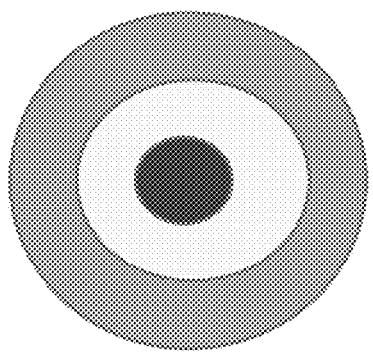
Figure 6:
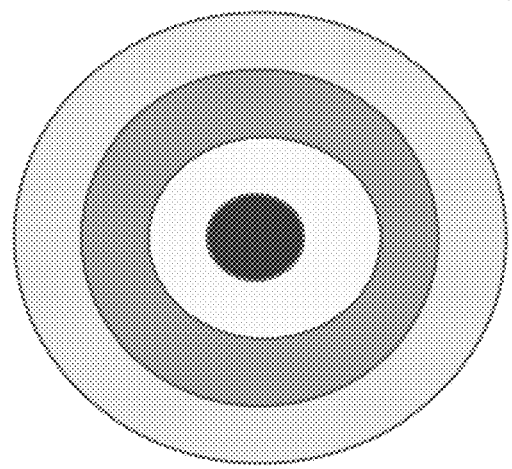
Figure 7:
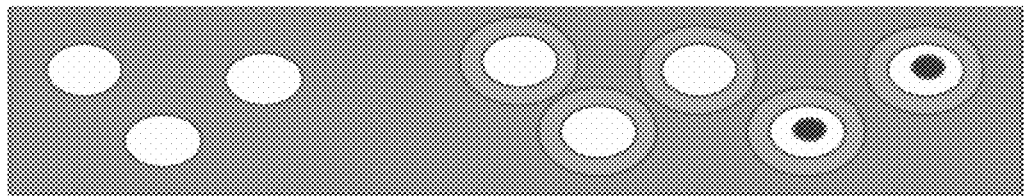
FIG. 7 shows pictorially examples of composites.
Figure 8:
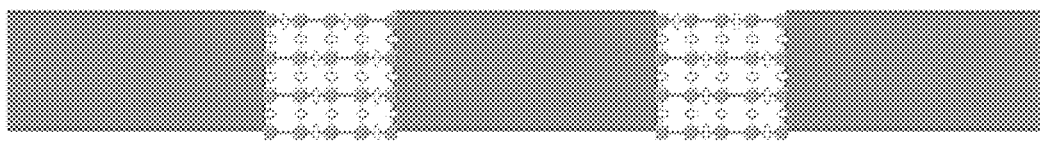
FIG. 8 shows pictorially examples of a membrane.
Figure 8:
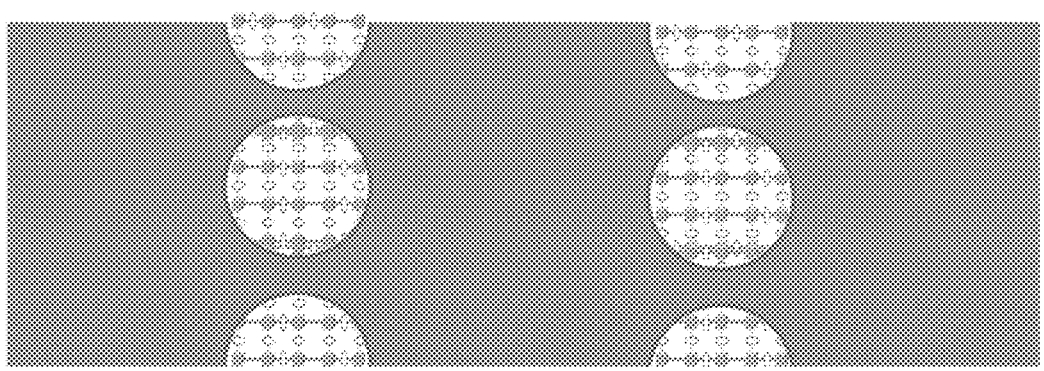

Various materials can be obtained using and/or incorporating a multi-dimensional networks described herein. For example, a multi-dimensional network as described herein (such as a network that can include a recurring unit of Formula (I) and a recurring unit of Formula (II)) can be used and/or incorporated into a powder, composite, film and/or fiber. Additionally, in some embodiments, networks described herein can be interpertrated into another network. In other embodiments, a network described herein can be layered and/or contained (partially and/or completely) in another network and/or non-network material. FIG. 6 shows pictorially examples of networks with variable functionality (for example, porosity) and/or structure (for example, one network contained within another network or a non-network material). FIGS. 7 and 8 pictorially show examples of composites and membranes.

The multi-dimensional networks (e.g., EMFs) described herein may be prepared in various ways. General synthetic routes for preparing EMFs and some examples of starting materials used to synthesize EMFs are described herein. The routes shown and described herein are illustrative only and are not intended, nor are they to be construed, to limit the scope of the claims in any manner whatsoever. Those skilled in the art, in view of the guidance provided herein, will be able to recognize modifications of the disclosed syntheses and to devise alternate routes based on the disclosures herein; all such modifications and alternate routes are within the scope of the claims.

In some embodiments, the metal oxides, metal nitrates and/or metal ions (hereinafter referred to as "metal-containing starting material") can be combined in a solution with recurring units of Formula (II), wherein the recurring units of Formula (II) have one or more hydrogens and/or leaving groups associated with the atoms that become attached to the recurring units of Formula (I) (hereinafter referred to as "Formula (II) starting material"). When the network comprises two different recurring units of Formula (I), a first amount of a first metal-containing starting material and a second amount of a second metal-containing starting material can be combined with a Formula (II) starting material. The first amount and the second amount can be the same or different. Similarly, when the network comprises two different recurring units of Formula (II), a first amount of a first Formula (II) starting material and a second amount of a second Formula (II) starting material can be combined with a metal-containing starting material. The resulting networks can be isolated and purified using methods known to those skilled in the art informed by the guidance provided herein.

The networks described herein can be used for various uses and applications. Some embodiments described herein related to the use of a network described herein for gas purification. Other embodiments described herein related to the use of a network described herein for gas separation. Still other embodiments described herein related to the use of a network described herein for gas storage, such as hydrogen storage. Yet still other embodiments described herein related to the use of a network described herein for catalysis. For example, a network described herein can be used as a catalyst and/or can be used to deliver a catalyst (for example, a metal-based catalyst). Some embodiments described herein related to the use of a network described herein for treatment or amelioration of a disease or condition. Other embodiments described herein related to the use of a network described herein for diagnosing a disease or condition. Some embodiments described herein related to the use of a network described herein for magnetic devices. Some embodiments described herein related to the use of a network described herein for electro-optical devices. Some embodiments described herein related to the use of a network described herein for chemo-optical devices. Some embodiments described herein related to the use of a network described herein as an electrode. Some embodiments described herein related to the use of a network described herein for a photoelectrode.

EXAMPLES

Additional embodiments are disclosed in further detail in the following examples, which are not in any way intended to limit the scope of the claims.

Synthesis of polypeptide based links with $Zn_4O(CO_2)_6$ joints. The networks described herein can be prepared by mixing varied amounts of chemically functionalized amino acid links with zinc nitrate in N,N-diethylformamide (DEF) or N,N-dimethylformamide (DMF) in an oven for 24 hrs. The temperature can be between about 25° C. to 160° C. to optimize yield and crystallinity. Acid or base (such as acetic acid and triethylamine) can be added to control the pH of the starting solution. The resultant crystalline material is then immersed in DEF for 24 hrs, and then sequentially in chloroform for three 24 hr periods. The material is activated by removing the solvent under vacuum for 24 hrs at room temperature or heat up to 120° C.

Alternatively, the networks described herein can be prepared by mixing varied amounts of chemically functionalized amino acids link with zinc nitrate in 1-methyl-2-pyrrolidinone (NMP) and N,N-dimethylformamide (DMF) solvent mixture in oven for 24 hrs. The temperature can be between about 25° C. to 120° C. to optimize yield and crystallinity. Acid or base (such as acetic acid and triethylamine) can be added to control the pH of the starting solution. The resultant crystalline material is then immersed in DEF for 24 hrs and then sequentially in chloroform for three 24 hr periods. The material is activated by removing the solvent under vacuum for 24 hrs at room temperature or heat up to 120° C.

Using photolysible links or joints, materials with transformable properties may be synthesized. A transformable functionally active membrane comprising a recurring unit of Formula (I) and a recurring unit of Formula (II) is prepared as a polypeptide based extended material using a photolysible unit inserted within the polypeptide link. An example of a photolysible unit inserted within the polypeptide link is shown below.

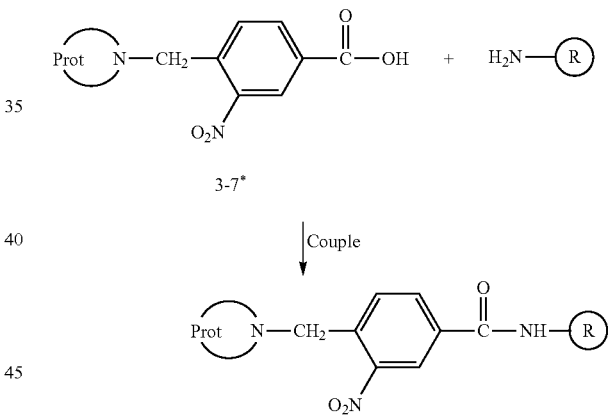

In the resulting material, such a network described herein, the link may be selectively cleaved with light (350 nm) at the ortho-nitrobenzylamide linkage.

Synthesis of a transparent film of tungsten oxide polyoxometalates based joints with conducting polythiophene links coordinated to the tungstate joint via dicarboxylate functionalization on to a conducting carboxylate terminated indium tin oxide transparent conducting layer on glass. The film can allow for cation intercalation and/or reduction of the tungsten to change the film's index of refraction as an electrochromic material.

A functionally active fiber can be synthesized by first preparing a network described herein that includes a recurring unit of Formula (I) and a recurring unit of Formula (II) in a nanoparticulate form (powder). The nanoparticulate form can be added to a polymer fiber or film or bulk solid. The resulting composite can have functional properties bestowed by the presence of a material that includes a recurring unit of Formula (I) and a recurring unit of Formula (II). Pictorial examples of a composite is shown in FIG. 7.

The composite can be prepared by mixing varied amounts of chemically functionalized amino acid links with zinc nitrate in N,N-diethylformamide (DEF) or N,N-dimethylformamide (DMF) in oven for 24 hrs. The temperature can be between about 25° C. to 160° C. to optimize yield and crystallinity. Acid or base (such as acetic acid and triethylamine) can be added to control the pH of the starting solution. The resultant crystalline material can be then immersed in DEF for 24 hrs, and then sequentially in chloroform for three 24 hr periods. The resulting material can be activated by removing the solvent under vacuum for 24 hrs at room temperature or heat up to 120° C. The powder material is then ball milled to obtain nanoparticulates of approximately 50 nm in size. The dry powder is mixed (5 wt %) with commercial Poly(butylene terephthalate) (PBT) powder, and the composite prepared by meltblending in a Haake Rheometer equipped with the intermeshing corotating type of a twin-screw. The temperature of the heating zone, from the hopper to the die, is set to 250° C., and the screw speed is fixed at 45 rpm. Upon completion of melt blending, the extruded fibers are cooled in a water bath.

A battery electrode can be formed from conducting high surface area powder that includes a network described herein (for example, a network that includes a recurring unit of Formula (I) and a recurring unit of Formula (II)). The material can be prepared by copolymerization of the conducting link dicarboxylated pyrrole with metal ions. The structure of the pyrrole is shown below.

Triethylamine can be added to a solution with a mixture of Mn, Fe, and Cu nitrates in N,N'-dimethylformamide (DMF)/chlorobenzene. The dicarboxylate can be deprotonated and react with the metal. Hydrogen peroxide may be added to facilitate the formation of $O^{2-}$ in the self-forming joint. The mixture is heated for 24 hours at 100° C. Acetic acid can be added to control the pH value of the starting solution. The resultant crystalline material can be then immersed in DEF for 24 hrs, and then sequentially in chloroform for three 24 hr periods. The resulting material can be activated by removing the solvent under vacuum for 24 hrs at room temperature or heat up to 120° C.

A functionally active conducting membrane that includes a network described herein (for example, a network that includes a recurring unit of Formula (I) and a recurring unit of Formula (II)) can be prepared by carboxylating the transparent conducting oxide indium tin oxide (ITO) substrate, and reacting the substrate with a mixture of copper and iron nitrates together with the dicarboxylated pyrrole which serves as the conducting linker.

A functionally active membrane that includes a network described herein (for example, a network that includes a recurring unit of Formula (I) and a recurring unit of Formula (II)) can be prepared by carboxylating the surface of a microporous alumina membrane. The pores of the membrane can then be filled with a network described herein (for example, a network that includes a recurring unit of Formula (I) and a recurring unit of Formula (II)). A pictorial example of a membrane that includes a network described herein is shown in FIG. 8.

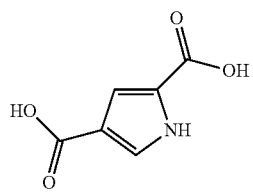

Example 1

Preparation of BDC-Amino-Gly-Boc and BDC-Amino-Ala-Boc

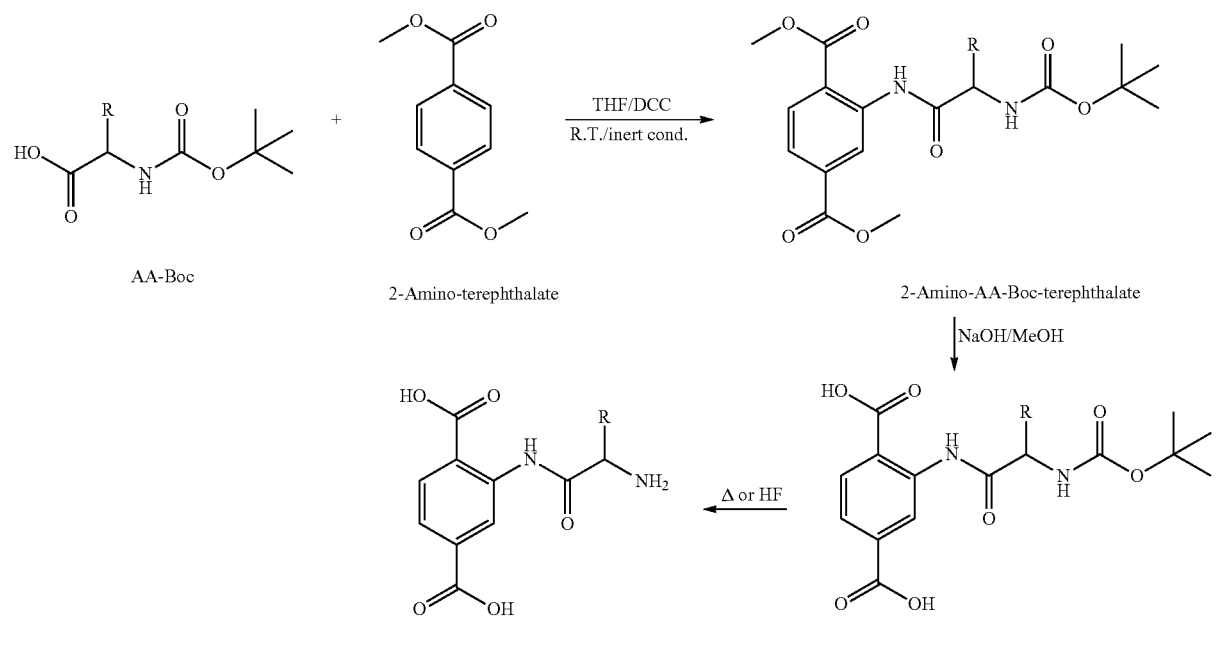

The amino portion of the amino acid was protected with a suitable protecting group, such as tert-Butyloxycarbonyl (BOC) or 9-Fluorenylmethyloxycarbonyl (Fmoc) using methods known to those skilled in the art. The amino-protected amino acid was reacted with 2-amino terephthalate at room temperature in THF using a coupling reagent, for example, N,N'-dicyclohexylcarbodiimide (DCC). The ester groups on the phenyl ring were hydrolyzed to carboxylic acid groups using NaOH to form 2-amino-AA-Boc terephthalic acid. The protecting group on the amino group of the amino acid was removed using heat or HF to give the product. The starting amino acids were glycine and alanine.

Figure 10:
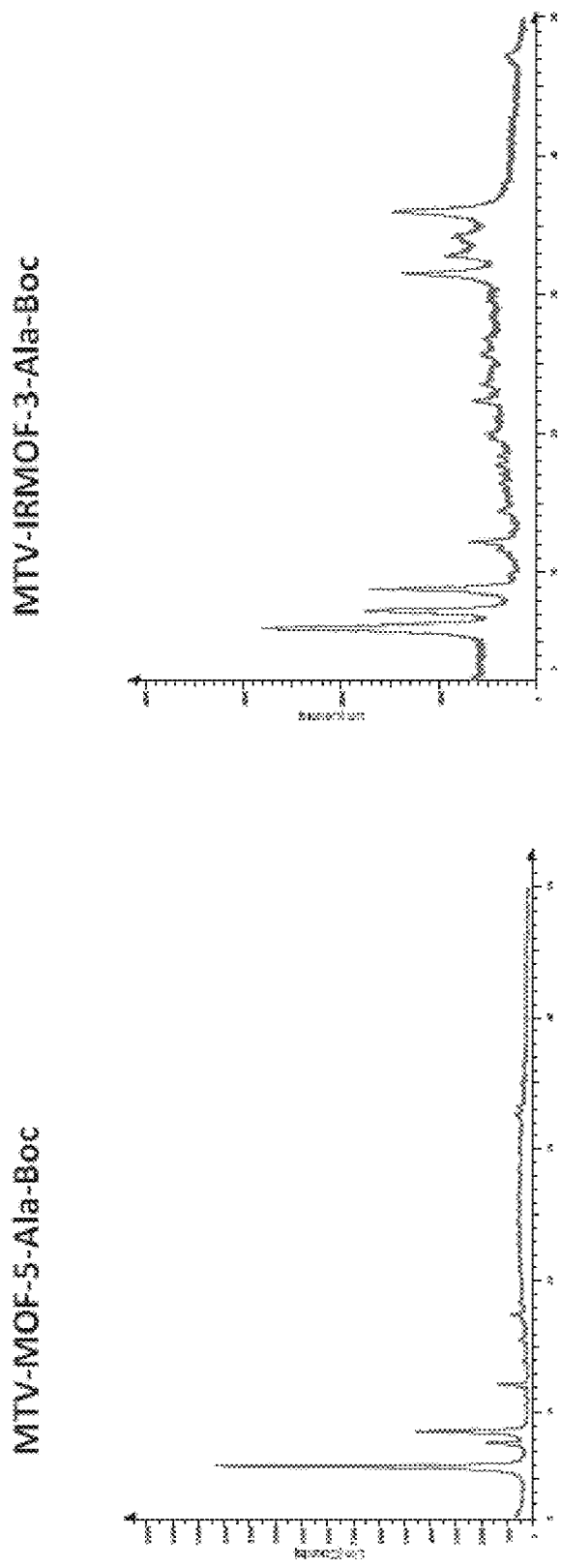
FIG. 10 shows the powder diffraction spectra for MTV-MOF-5-Ala-Boc and MTV-IRMOF-3-Ala-Boc.

The multi-dimensional network containing the linkers from Example 1 were synthesized according to the procedure proteded in Deng et al., Science (2010) 327:846-850, which is hereby incorporated by reference in its entirety. The linker obtained from Example 1 was protected with a suitable protecting group, for example, Boc or Fmoc. The protected linker was dissolved with a metal salt (for example, $Zn(NO_3)_2 \cdot 6H_2O$) in DMF. The mixture was heated to 85° C. for 48 hours. The heat was then increased to 120° C. to remove the protecting group. The product network was characterized by powder diffraction. The powder diffraction patterns for MTV-MOF-5-Ala-Boc and MTV-IRMOF-3-Ala Boc are provided in FIG. 10.

Example 2

Preparation of Networks with Amino Acids (Mosaic 1 and Mosaic 2)

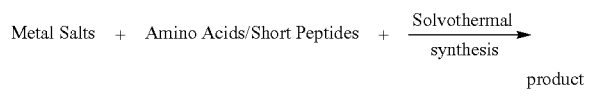

Figure 11:
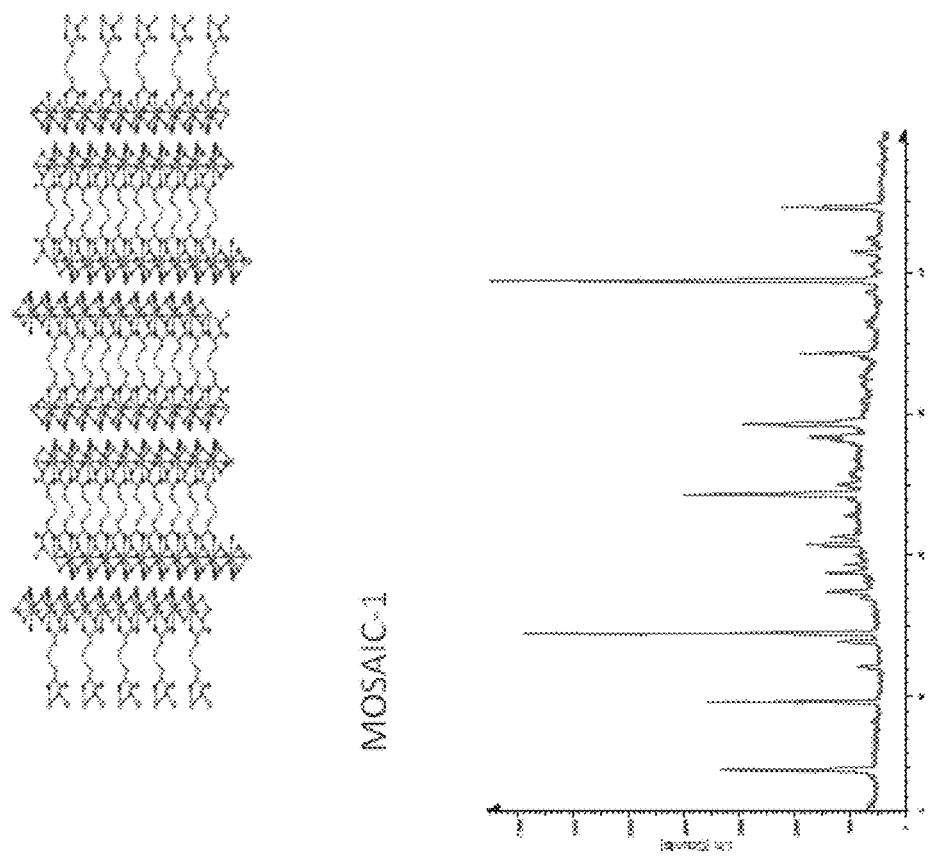
FIG. 11 shows a reaction scheme for preparing Mosaic 1, a ball and stick representation of Mosaic 1, a magnified portion of Mosaic 1 and powder diffraction spectrum for Moisaic 1.

Preparation of Mosaic 1:

114 mg of Ca(NO3)2.4H2O (0.48 mmol) were dissolved in 4 mL MeOH. 27 mg of (Cys)$_2$ (0.11 mmol) were dissolved in 1 mL H$_2$O and 5 drops of NaOH 2M. The two clear solutions were combined in a 20 mL vial and placed in a programmable oven with a program of ramp to 85° C. at a rate of 2 deg/min and cooled to room temperature at a rate of 0.1 deg/min yielding colorless plate crystals. Data for x-ray powder diffraction were collected by using a D8-Advance diffractometer (Bruker) in reflectance Bragg-Brentano geometry employing Ni-filtered CuKα line focused radiation at 1,600 W (40 kV, 40 mA) power and equipped with a Na (Tl) scintillation detector fitted with a 0.2-mm radiation entrance slit. Data for single crystal diffraction were collected on a Bruker SMART APEXII three circle diffractometer equipped with a CCD area detector and operated at 1200 W power (40 kV, 30 mA) to generate Cu Kα radiation (λ=1.5418 Å). The structure was solved by SHELXTL software package. The reaction scheme, a ball and stick representation of the network, a magnified portion of the network and powder diffraction is shown in FIG. 11. As shown in FIG. 11, aliphatic carboxylates bridge between Ca$^{2+}$ ions. The amino and carboxylate groups from the amino acid are coordinated to the Ca$^{2+}$ as well as to a nitrate (NO$_3^-$). The recurring units of Formula (I) in Mosaic 1 are SBU, which is a rod type of $Ca_2O_6N_2H_2$.

Figure 12A:
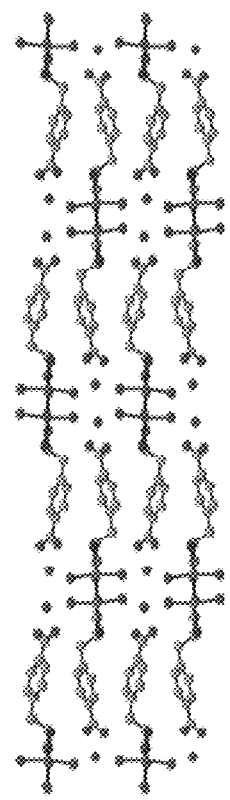
FIGS. 12A and 12B show a reaction scheme for preparing Mosaic 2, a ball and stick representation of Mosaic 2, 2 different magnified portions of Mosaic 2 and powder diffraction spectrum for Moisaic 2.
Figure 12A:
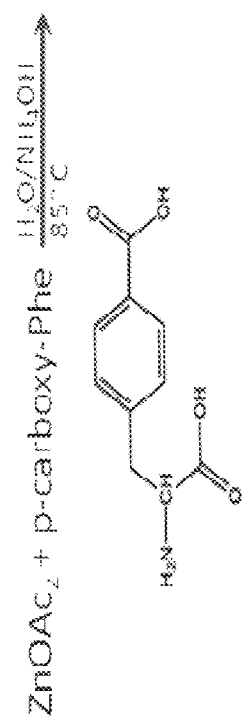
Figure 12B:
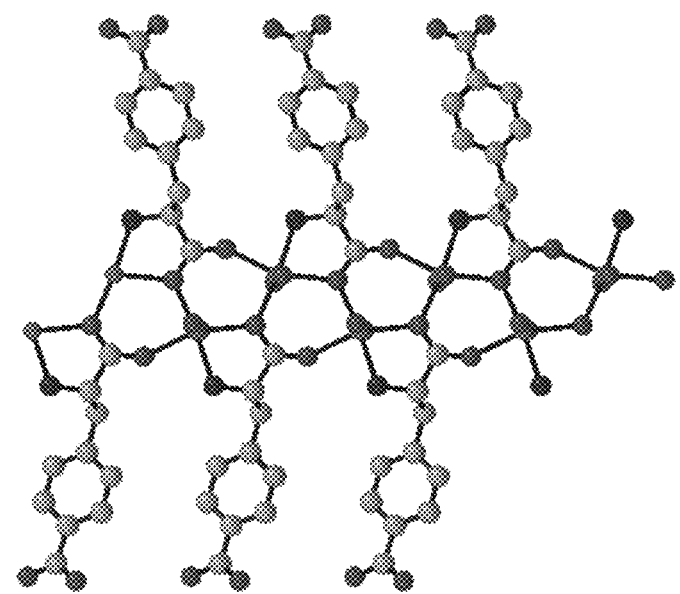
Figure 12B:
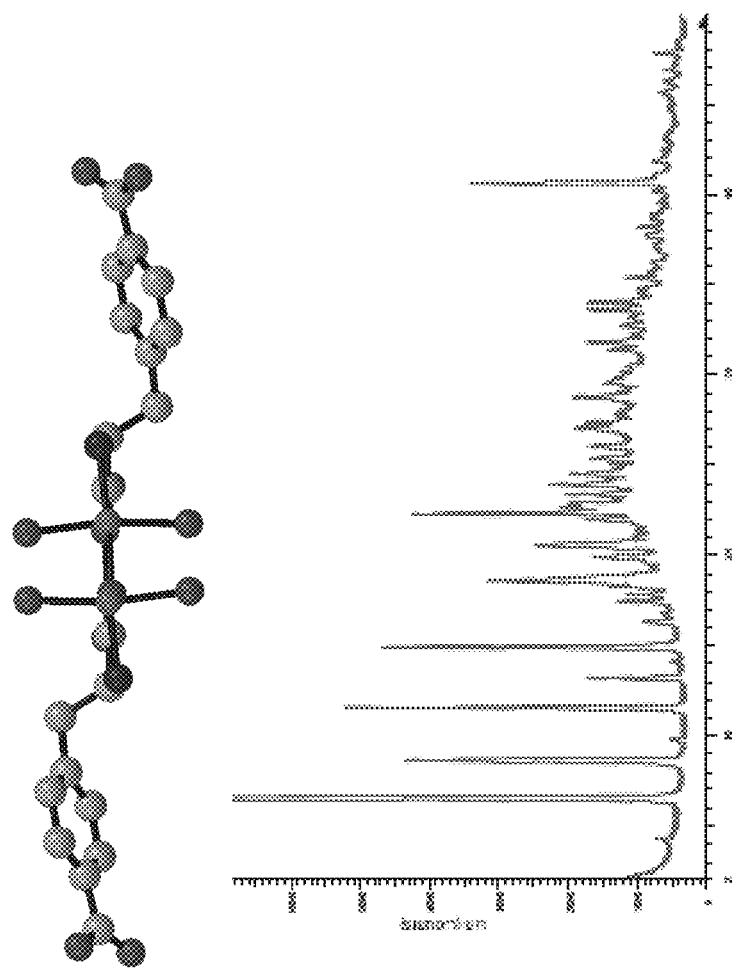

Preparation of Mosaic 2:

In a 4 mL vial, 8.06 mg (0.033 mmol) of p-carboxy-Phe were dissolved in 1000 μL of H$_2$O and 20 μL of NH$_4$OH. The solution was sonicated for 5 minutes to form a clear solution. 6.88 mg of ZnOAc2 (0.037 mmol) were added to the solution and placed in an isothermal oven of 85° C. for 24 hrs, which yielded a colorless plate crystals. Data for x-ray powder diffraction were collected by using a D8-Advance diffractometer (Bruker) in reflectance Bragg-Brentano geometry employing Ni-filtered CuKα line focused radiation at 1,600 W (40 kV, 40 mA) power and equipped with a Na (Tl) scintillation detector fitted with a 0.2-mm radiation entrance slit. Data for single crystal diffraction were collected on a Bruker SMART APEXII three circle diffractometer equipped with a CCD area detector and operated at 1200 W power (40 kV, 30 mA) to generate Cu Kα radiation (λ=1.5418 Å). The structure was solved by SHELXTL software package. The reaction scheme, a ball and stick representation of the network, two different magnified portions of the network, and powder diffraction is shown in FIGS. 12A and 12B. Aliphatic carboxylates bridge between Zn$^{2+}$ ions, and the amino and carboxylate groups from the amino acid are coordinated to the Zn$^{2+}$. The aromatic carboxylate attached to the phenyl ring is free. The recurring units of Formula (I) in Mosaic 1 are SBU, which is a rod type of $ZnO_5NH_4$ Example 3

Preparation of Networks with Amino Acids (Mosaic 3)

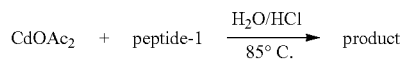

Peptide-1 was prepared according to methods known to those skilled in the art. Peptide-1 has the sequence: H-Glu-Phe(p-carboxy)-Phe(p-carboxy)-Ala-Gly-OH (SEQ. ID: 1), and the structure is shown below.

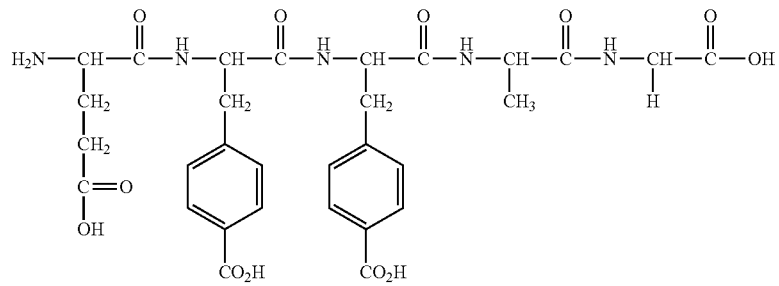 [SMILES: CC(NC(=O)C(Cc1ccc(C(=O)O)cc1)NC(=O)C(Cc1ccc(C(=O)O)cc1)NC(=O)C(N)CCC(=O)O)C(=O)NCC(=O)O]

Figure 13:
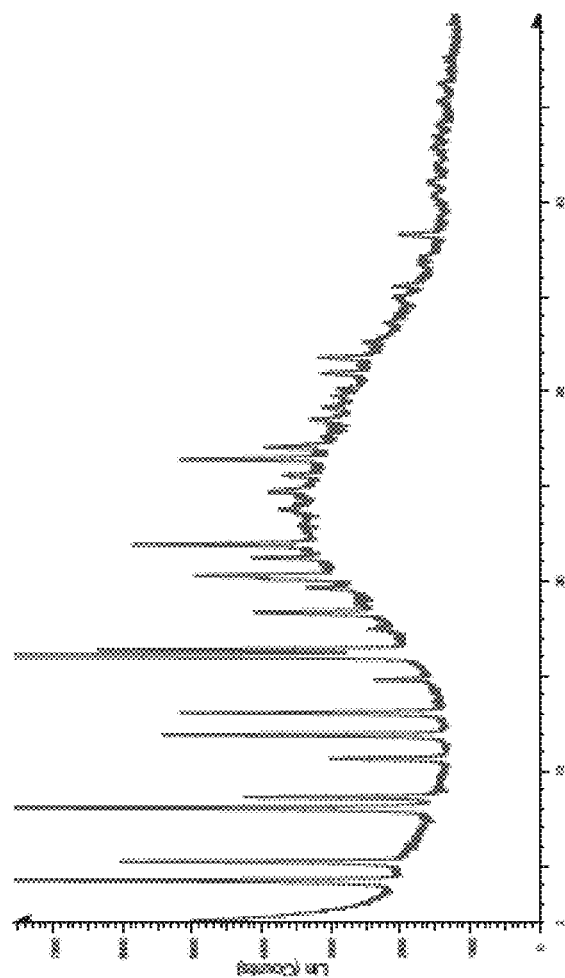
FIG. 13 shows the powder diffraction spectrum for Mosaic 3.

Preparation of Mosaic 3:

In a 4 mL vial, 3 mg (0.0045 mmol) of Peptide-1 were dissolved in 1000 μL of H$_2$O and 0.13 μL of HCl. The solution was sonicated for 5 minutes to form a clear solution. 2.99 mg of CdOAc$_2$.2H$_2$O (0.011 mmol) were added to the solution, and the vial was placed in an isothermal oven of 85° C. for 24 hrs, which yielded colorless needle crystals. Data for x-ray powder diffraction were collected by using a D8-Advance diffractometer (Bruker) in reflectance Bragg-Brentano geometry employing Ni-filtered CuKα line focused radiation at 1,600 W (40 kV, 40 mA) power and equipped with a Na (Tl) scintillation detector fitted with a 0.2-mm radiation entrance slit. The powder diffraction pattern indicates a formation of an extended structure according to the number and position of peaks. The powder diffraction is shown in FIG. 13.

Example 4

Preparation of Networks with Amino Acids and Metal Ions Linkers (Mosaic 4)

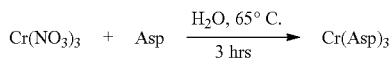

Preparation of Cr(Asp)$_3$:

5.22 mg (0.0045 mmol) of aspartic acid (Asp) were dissolved in 8 mL of H$_2$O in a 20 mL vial. To the clear solution were added 270 μL of Cr(NO$_3$)$_3$.9H$_2$O solution in DMF. The solution was placed in an isothermal oven of 65° C. for 3 hrs, which yielded a color change to crimson. The color changed indicated the formation of the Cr(Asp)$_3$. The solvent was allowed to evaporate to form a crimson solid. The solid was collected in a quantitative yield of >95%.

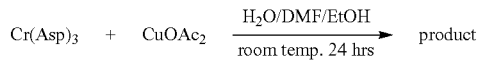

Figure 14:
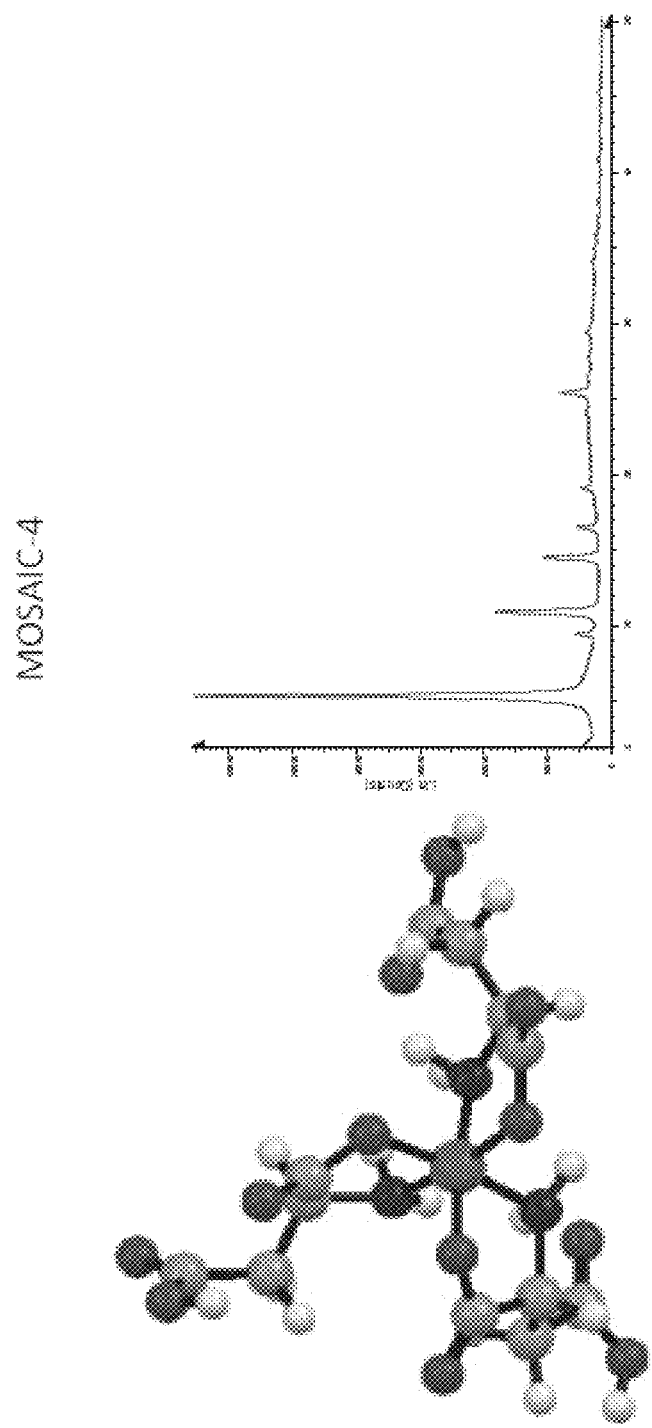
FIG. 14 shows a ball and stick representation of a linker of Mosaic 4 and powder diffraction spectrum for Mosaic 4.

Preparation of Mosaic 4:

Cr(Asp)$_3$, which was obtained and dried before use, was redissolved in 12 mL of a mixture of MeOH/H$_2$O/DMF 1:1:1 and 6 mL were used. To the clear solution were added 2 equivalents of CuOAc$_2$ 17.01 mg (0.085 mmol). Data for x-ray powder diffraction were collected by using a D8-Advance diffractometer (Bruker) in reflectance Bragg-Brentano geometry employing Ni-filtered CuKα line focused radiation at 1,600 W (40 kV, 40 mA) power and equipped with a Na (Tl) scintillation detector fitted with a 0.2-mm radiation entrance slit. Data for single crystal diffraction were collected on a Bruker SMART APEXII three circle diffractometer equipped with a CCD area detector and operated at 1200 W power (40 kV, 30 mA) to generate Cu Kα radiation (λ=1.5418 Å). The structure was solved by SHELXTL software package. A ball and stick representation of the linker and powder diffraction is shown in FIG. 14.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A multi-dimensional network comprising:
   a first recurring unit having the structure of Formula (I); and
   a second recurring unit having the structure of Formula (II):

wherein:
J is a first group that comprises at least one selected from the group consisting of a metal ion, a carbon atom and an organic-based group;
A is selected from the group consisting of a bond, oxygen, sulfur, phosphorus, selenium and arsenic;

n is an integer ≥3;

L is a second group that comprises at least one selected from the group consisting of an optionally substituted amino acid, an optionally substituted amino acid ester, an optionally substituted carbohydrate and an optionally substituted nucleic acid;

wherein the number of recurring units of Formula (II) connected to each recurring unit of Formula (I) is equal to n;

wherein if A is a bond, the number of recurring units of Formula (II) connected to J is equal to n; and wherein in the recurring unit of Formula (I), the number of A groups attached to each J is equal to n, and each A in the recurring unit of Formula (I) cannot be connected to another A.

2. The multi-dimensional network of claim 1, wherein the metal ion is a metal selected from any of Groups Ia, IIa, IIIa, IVa, Va, VIa, VIIa, VIIIa, Ib, IIb, IIIb, IVb, Vb, VIb, VIIb, VIIb and VIII of the periodic table.

3. The multi-dimensional network of claim 1, wherein the metal ion is selected from the group consisting of: $Mg^{+2}$, $Ca^{+2}$, $Sr^{+2}$, $Ba^{+2}$, $Sc^{+3}$, $Y^{+3}$, $Ti^{+4}$, $Zr^{+4}$, $Hf^{+4}$, $V^{+4}$, $V^{+3}$, $V^{+2}$, $Nb^{+3}$, $Ta^{+3}$, $Cr^{+3}$, $Mo^{+3}$, $W^{+3}$, $Mn^{+3}$, $Mn^{+3}$, $Re^{+3}$, $Re^{+2}$, $Fe^{+3}$, $Fe^{+2}$, $Ru^{+3}$, $Ru^{+2}$, $Os^{+3}$, $Os^{+2}$, $Co^{+3}$, $Co^{+2}$, $Rh^{+2}$, $Rh^+$, $Ir^{+2}$, $Ir^+$, $Ni^{+2}$, $Ni^+$, $Pd^{+2}$, $Pd^+$, $Pt^{+2}$, $Pt^+$, $Cu^{+2}$, $Cu^+$, $Ag^+$, $Au^+$, $Zn^{+2}$, $Cd^{+2}$, $Hg^{+2}$, $Al^{+3}$, $Ga^{+3}$, $In^{+3}$, $Tl^{+3}$, $Si^{+4}$, $Si^{+4}$, $Si^{+2}$, $Ge^{+4}$, $Ge^{+2}$, $Sn^{+4}$, $Sn^{+2}$, $Pb^{+4}$, $Pb^{+2}$, $As^{+5}$, $As^{+3}$, $As^+$, $Sb^{+5}$, $Sb^{+3}$, $Sb^+$, $Bi^{+5}$, $Bi^{+3}$ and $Bi^+$.

4. The multi-dimensional network of claim 1, wherein at least one metal ion is $Zn^{+2}$.

5. The multi-dimensional network of claim 1, wherein the recurring units of Formula (I) are the same.

6. The multi-dimensional network of claim 1, comprising two different recurring units of Formula (I).

7. The multi-dimensional network of claim 1, comprising three different recurring units of Formula (I).

8. The multi-dimensional network of claim 1, comprising four different recurring units of Formula (I).

9. The multi-dimensional network of claim 1, comprising five or more different recurring units of Formula (I).

10. The multi-dimensional network of claim 1, wherein the recurring units of Formula (II) are the same.

11. The multi-dimensional network of claim 1, comprising two different recurring units of Formula (II).

12. The multi-dimensional network of claim 1, comprising three different recurring units of Formula (II).

13. The multi-dimensional network of claim 1, comprising four different recurring units of Formula (II).

14. The multi-dimensional network of claim 1, comprising five or more different recurring units of Formula (II).

15. The multi-dimensional network of claim 1, wherein L does not include an optionally substituted aryl, an optionally substituted cycloalkyl or an optionally substituted cycloalkenyl group.

16. The multi-dimensional network of claim 1, wherein L does not include an optionally substituted phenyl group.

17. The multi-dimensional network of claim 1, wherein L comprises an optionally substituted amino acid.

18. The multi-dimensional network of claim 1, wherein L comprises an optionally substituted amino acid ester.

19. The multi-dimensional network of claim 17, wherein the amino acid is selected from α-amino acids, β-amino acids, γ-amino acids and δ-amino acids.

20. The multi-dimensional network of claim 17, wherein the amino acid is selected from alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine.

21. The multi-dimensional network of claim 17, wherein the amino acid includes a second moiety.

22. The multi-dimensional network of claim 21, wherein the amino acid includes a third moiety.

23. The multi-dimensional network of claim 1, wherein L comprises an optionally substituted amino acid and a metal ion.

24. The multi-dimensional network of claim 17, wherein a portion of the optionally substituted amino acid extends into one or more pores of the multi-dimensional network.

25. The multi-dimensional network of claim 1, wherein L comprises a nucleic acid.

26. The multi-dimensional network of claim 25, wherein the nucleic acid is DNA or RNA.

27. The multi-dimensional network of claim 1, wherein L comprises a carbohydrate.

28. The multi-dimensional network of claim 1, wherein L comprises one or more substituents not attached to a recurring unit of Formula (I).

29. The multi-dimensional network of claim 1, wherein the network has functionality as a result of cooperative interactions between one or more of the recurring units of Formula (I) and/or one or more recurring units of Formula (II).

30. The multi-dimensional network of claim 1, wherein the network has functionality as a result of cooperative interactions between one or more of the recurring units of Formula (I) and/or one or more recurring units of Formula (II), wherein the cooperative interactions are configured to be capable of being turned on by an external field.

31. The multi-dimensional network of claim 30, wherein the external field is selected from the group consisting of magnetic, electric, optical and thermal.

32. The multi-dimensional network of claim 1, wherein the arrangement of one or more of the recurring units of Formula (I) and/or one or more recurring units of Formula (II) encodes information.

33. The multi-dimensional network of claim 32, wherein the arrangement of one or more of the recurring units of Formula (I) and/or one or more recurring units of Formula (II) is regular or random.

34. The multi-dimensional network of claim 1, wherein the network is in a form selected from the group consisting of a powder, a film and a composite.

35. The multi-dimensional network of claim 1, wherein network is partially or completely contained in a material or supported on a material.

36. The multi-dimensional network of claim 35, wherein the material is selected from the group consisting of a metal substrate and an alumina membrane.

37. The multi-dimensional network of claim 1, wherein the network is included in an electrode.

38. The multi-dimensional network of claim 1, wherein the network is included in an electrochromic coating.

39. The multi-dimensional network of claim 1, wherein the network is included in a material selected from the group consisting of an absorber, an active or passive optical device, an active or passive electronic device and a chemo-optical sensor.

* * * * *